US012569226B2

(12) United States Patent
Xie et al.

(10) Patent No.: US 12,569,226 B2
(45) Date of Patent: Mar. 10, 2026

(54) ULTRASOUND SYSTEM AND METHOD FOR GUIDED SHEAR WAVE ELASTOGRAPHY OF ANISOTROPIC TISSUE

(71) Applicant: KONINKLIJKE PHILIPS N.V., Eindhoven (NL)

(72) Inventors: Hua Xie, Cambridge, MA (US); Grzegorz Andrzej Toporek, Boston, MA (US); Gary Cheng-How Ng, Redmond, WA (US); Vijay Thakur Shamdasani, Kenmore, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 424 days.

(21) Appl. No.: 17/262,390

(22) PCT Filed: Jul. 22, 2019

(86) PCT No.: PCT/EP2019/069618
§ 371 (c)(1),
(2) Date: Jan. 22, 2021

(87) PCT Pub. No.: WO2020/020802
PCT Pub. Date: Jan. 30, 2020

(65) Prior Publication Data
US 2021/0290203 A1 Sep. 23, 2021

Related U.S. Application Data

(60) Provisional application No. 62/702,793, filed on Jul. 24, 2018.

(51) Int. Cl.
*A61B 8/00* (2006.01)
*A61B 8/08* (2006.01)
(Continued)

(52) U.S. Cl.
CPC ............ *A61B 8/485* (2013.01); *A61B 8/0883* (2013.01); *A61B 8/4254* (2013.01); *A61B 8/467* (2013.01);
(Continued)

(58) Field of Classification Search
CPC ..... A61B 8/485; A61B 8/0883; A61B 8/4254; A61B 8/467; A61B 8/483; G01S 7/52053; G01S 15/8934; G01S 15/8993
See application file for complete search history.

(56) References Cited

U.S. PATENT DOCUMENTS 5,159,931 A * 11/1992 Pini .......................... A61B 8/14
600/443
6,443,896 B1 9/2002 Detmer
(Continued)

FOREIGN PATENT DOCUMENTS

WO 2004021040 A1 3/2004
WO 2019155037 A1 2/2018

OTHER PUBLICATIONS

*Wang et al., "Imaging Transverse Isotropic Properties of Muscle by Monitoring Acoustic Radiation Force Induced Shear Waves using a 2D Matrix Ultrasound Array", IEEE Transactions on Medical Imaging, vol. 32, No. 9, 2013, 1671-1684 (Year: 2013).*
(Continued)

*Primary Examiner* — Keith M Raymond
*Assistant Examiner* — Andrew W Begeman

(57) ABSTRACT

The present disclosure includes ultrasound systems and methods for imaging anisotropic tissue with shear wave elastography at a variety of angles with respect to the tissue. An example ultrasound imaging system includes a probe coupled to a position tracking system for tracking a position of the probe with respect to a subject, and a processor in communication with the probe. The processor may receive
(Continued)

position tracking data from the position tracking system. The processor may define at least one target plane in anisotropic tissue, determine a difference between a current position of the probe and the position of the target plane, and provide a visual indicator of the difference, wherein the processor dynamically updates the visual indicator responsive to a change in the position of the imaging plane with respect to the target plane.

27 Claims, 12 Drawing Sheets

(51) Int. Cl.
   G01S 7/52 (2006.01)
   G01S 15/89 (2006.01)
(52) U.S. Cl.
   CPC .......... A61B 8/483 (2013.01); G01S 7/52053 (2013.01); G01S 15/8934 (2013.01); G01S 15/8993 (2013.01)

(56) References Cited

U.S. PATENT DOCUMENTS

| | | | | |
|---|---|---|---|---|
| 6,530,885 | B1 | 3/2003 | Entrekin et al. | |
| 2007/0010743 | A1* | 1/2007 | Arai | A61B 8/463 |
| | | | | 600/443 |
| 2007/0249935 | A1* | 10/2007 | Deschinger | A61B 8/0866 |
| | | | | 600/437 |
| 2008/0044054 | A1* | 2/2008 | Kim | A61B 8/466 |
| | | | | 382/100 |
| 2009/0060306 | A1* | 3/2009 | Ohuchi | A61B 8/0858 |
| | | | | 382/131 |
| 2009/0306509 | A1 | 12/2009 | Pedersen et al. | |
| 2010/0298704 | A1* | 11/2010 | Pelissier | A61B 8/0841 |
| | | | | 600/443 |
| 2011/0301460 | A1* | 12/2011 | Anite | A61B 8/4461 |
| | | | | 600/443 |
| 2011/0306025 | A1 | 12/2011 | Sheehan et al. | |
| 2013/0338505 | A1* | 12/2013 | Schneider | A61B 8/4455 |
| | | | | 600/444 |
| 2014/0081142 | A1* | 3/2014 | Toma | A61B 8/4245 |
| | | | | 600/443 |
| 2014/0371593 | A1* | 12/2014 | Kondoh | A61B 8/0858 |
| | | | | 600/443 |
| 2016/0143521 | A1 | 5/2016 | Eldon et al. | |
| 2016/0143621 | A1* | 5/2016 | Parthasarathy | G01S 7/52042 |
| | | | | 600/438 |
| 2016/0143622 | A1 | 5/2016 | Xie et al. | |

OTHER PUBLICATIONS

Aristizabal et al: "Shear Wave Vibrometry Evaluation in Transverse Isotropic Tissue Mimicking Phantoms and Skeletal Muscle"; Phys. Med. Biol. 59 (2014), pp. 7752.
Bird et al: "Characterization of Local Muscle Fiber Anisotropy Using Shear Wave Elastography in Patients With Chronic Myofascial Pain"; Annals of Physical and Rehabilitation Medicine 61S (2018), pp. e1-e102.
Chatelin et al: "Modelling the Impulse Diffraction Field of Shear Waves in Transverse Isotropic Viscoclastic Medium"; Physics in Medicine & Biology, vol. 60, No. 9, pp. 1-18.
Gennisson et al: "Viscoelastic and Anisotropic Mechanical Properties of in Vivo Muscle Tissue Assessed by Supersonic Shear Imaging"; Ultrasound in Med. & Biol, vol. 36, No. 5, pp. 789-801.
Lee et al: "Mapping Myocardial Fiber Orientation Using Echocardiography-Based Shear Wave Imaging"; IEEE Transactions on Medical Imaging, vol. 31, No. 3, Mar. 2012.
Miyamoto et al: "Validity of Measurement of Shear Modulus by Ultrasound Shear Wave Elastography in Human Pennate Muscle"; PLOS One, Apr. 8, 2015, pp. 1-11.
PCT/EP2019/069618 ISR & WO, Nov. 27, 2019 16 Page Document.
Taljanovic et al: "Shear-Wave Elastography: Basic Physics and Musculoskeletal Applications"; RSNA, 2017, pp. 885-870.
Wang et al: "Imaging Transverse Isotropic Properties of Muscle by Monitoring Acoustic Radiation Force Induced Shear Waves Using a 2-D Matrix Ultrasound Array"; IEEE Transactions on Medical Imaging, vol. 32, No. 9, Sep. 2013, pp. 1671-1684.

* cited by examiner

Fibers are in the imaging plane

Fibers are orthogonal to the imaging plane (a) Reference plane (b) Target plane (90°)

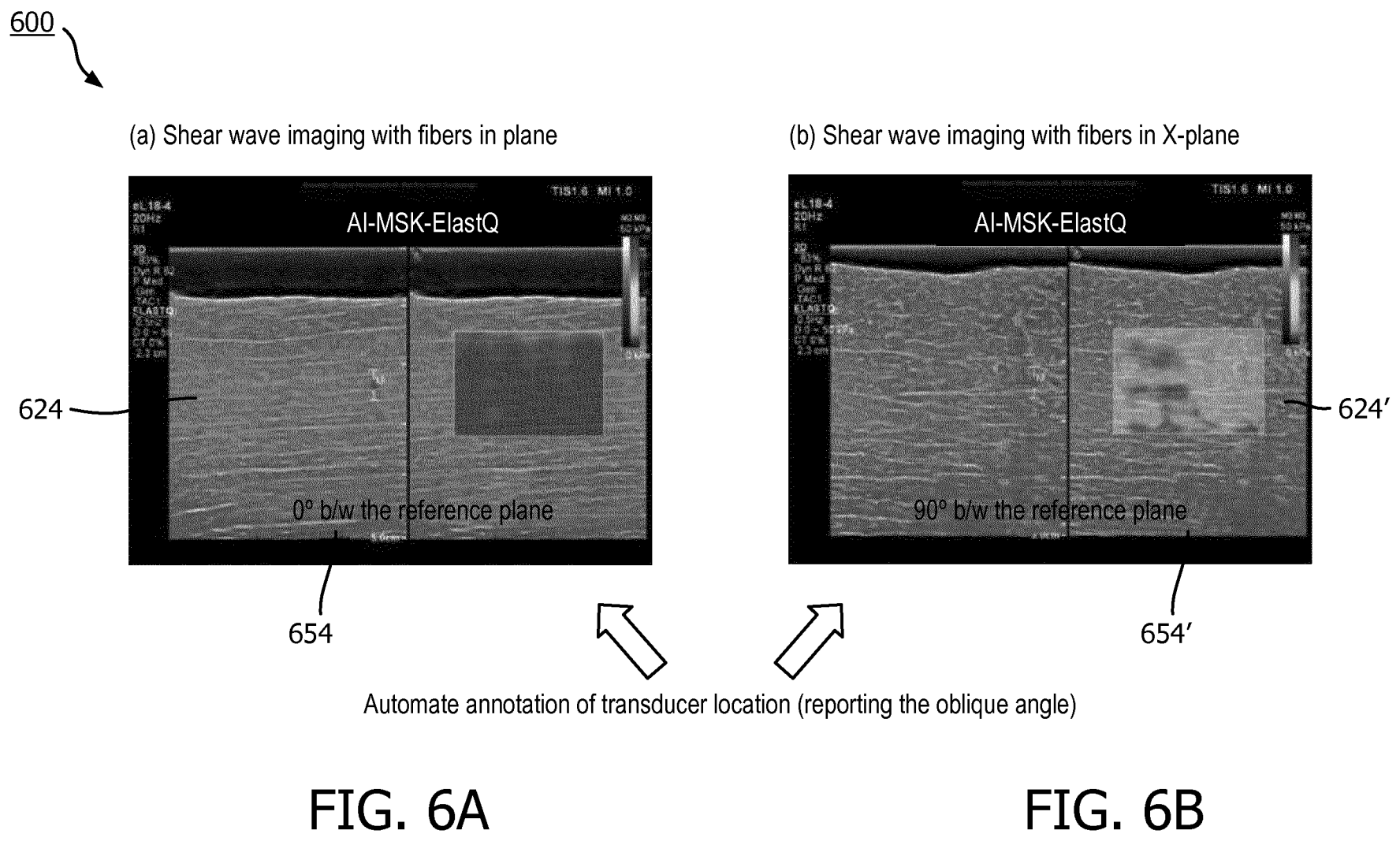

(a) Shear wave imaging with fibers in plane

FIG. 6A (b) Shear wave imaging with fibers in X-plane

FIG. 6B

Automate annotation of transducer location (reporting the oblique angle)

(b) Target plane

FIG. 7B (a) Reference plane

FIG. 7A

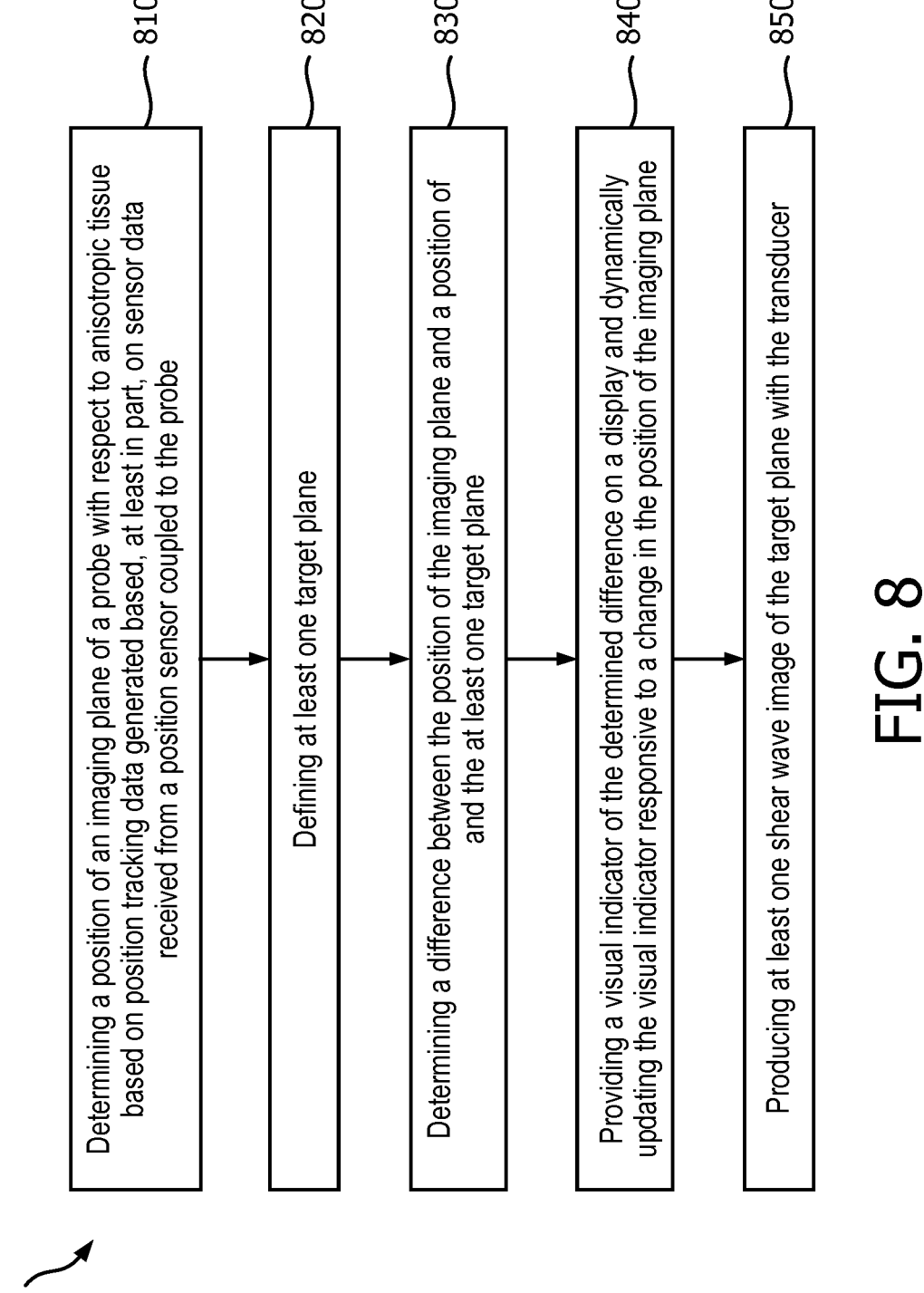

800

Determining a position of an imaging plane of a probe with respect to anisotropic tissue based on position tracking data generated based, at least in part, on sensor data received from a position sensor coupled to the probe — 810

Defining at least one target plane — 820

Determining a difference between the position of the imaging plane and a position of and the at least one target plane — 830

Providing a visual indicator of the determined difference on a display and dynamically updating the visual indicator responsive to a change in the position of the imaging plane — 840

Producing at least one shear wave image of the target plane with the transducer — 850

FIG. 8

ULTRASOUND SYSTEM AND METHOD FOR GUIDED SHEAR WAVE ELASTOGRAPHY OF ANISOTROPIC TISSUE

CROSS-REFERENCE TO PRIOR APPLICATIONS

This application is the U.S. National Phase application under 35 U.S.C. § 371 of International Application No. PCT/EP2019/069618, filed on Jul. 22, 2019, which claims the benefit of U.S. Provisional Patent Application No. 62/702,793, filed on Jul. 24, 2018. These applications are hereby incorporated by reference herein.

TECHNICAL FIELD

The present disclosure pertains to ultrasound systems and methods for imaging anisotropic tissue with shear wave elastography at a variety of angles with respect to the tissue.

BACKGROUND

An ultrasound imaging system, such as a cart-based ultrasound imaging system, typically includes a user interface, which operates in conjunction with a probe and a display to acquire and display images from a subject, such as a patient. The ultrasound imaging system may use shear wave elastography to determine mechanical properties of tissue. Shear wave elastography may be used for screening and diagnostic purposes such as to identify regions of abnormal stiffness in tissues, which may indicate the presence of for example, a tumor.

Different types of tissue have different properties. Certain types of tissue, such as liver tissue, may be generally isotropic, while certain other types of tissue, e.g., musculoskeletal, vascular wall, and myocardium tissue, may be anisotropic, where a property of the tissue (e.g., stiffness) may vary based on a direction along which that property is measured. In order to characterize the properties of an anisotropic tissue, measurements may need to be taken with the probe in more than one orientation with respect to the tissue. However, it may be difficult for an operator to precisely control or record the orientation of the probe. The examples described herein may provide solutions to one or more challenges in the field of guided anisotropic tissue imaging.

SUMMARY

The present disclosure pertains to ultrasound systems and methods for imaging anisotropic tissue with shear wave elastography at a variety of angles with respect to the tissue. In at least one aspect, the disclosure relates to an ultrasound imaging system for shear wave imaging. The ultrasound imaging system may include a probe and a processor. The probe may transmit and receive ultrasound echo signals for producing shear wave images of anisotropic tissue of a subject. The probe may be coupled to a position tracking system for tracking a position of the probe with respect to the subject. The processor may be in communication with the probe and configured to receive position tracking data from the position tracking system. The processor may define at least one target plane in the anisotropic tissue at an angle with respect to a reference plane of the anisotropic tissue. The processor may determine a difference between a first position of an imaging plane of the probe at the position indicated by the position tracking data and a second position of the at least one target plane. The processor may also provide a visual indicator of the difference on a display of the ultrasound system and dynamically update the visual indicator responsive to a change in the position of the imaging plane with respect to the target plane.

In at least one aspect, the disclosure relates to a of shear wave imaging. The method may include determining a position of an imaging plane of a probe with respect to anisotropic tissue based on position tracking data generated based, at least in part, on sensor data received from a position sensor coupled to the probe. The method may include defining at least one target plane and/or determining a difference between the position of the imaging plane and a position of the at least one target plane. The method may also include providing a visual indicator of the determined difference on a display and dynamically updating the visual indicator responsive to a change in the position of the imaging plane. The method may include producing at least one shear wave image of the target plane with the probe.

Aspects of the present disclosure, such as certain elements of the user interfaces described herein and/or functions performed by a processor of the ultrasound system, may be embodied in computer-readable media comprising processor-executable instructions. For example, processor-executable instructions for providing one or more graphical user interfaces or elements thereof may be incorporated into a software package, for example for execution on an analysis workstation. Aspects of the present disclosure may facilitate offline image analysis as described further below, however it will be understood that the principles described herein may be equally applied to online image analysis (e.g., analysis performed during or shortly after image acquisition). In accordance with one embodiment, a non-transitory computer-readable medium comprising processor-executable instructions for displaying ultrasound images may include instructions to display a first image frame from a first plurality of stored image files, wherein the image file contains first position information corresponding to a probe position during acquisition of the first image frame, receive, via a user interface, a request for an orthogonal view, compare the first position information with position information for a second plurality of stored image files to identify one or more images frames in the second plurality associated with position information closest to the first position information, and display a representation of each of the one or more image frames as candidate orthogonal views.

BRIEF DESCRIPTION OF THE DRAWINGS

FIGS. 6A and 6B are example shear wave elastography images of a muscular tissue including position indicators in accordance with some examples of the present disclosure.

FIGS. 7A and 7B are block diagrams of coordinate systems associated with the probe and anisotropic tissue in accordance with some examples of the present disclosure.

FIG. 8 is a flow chart depicting a method of guided shear wave elastography of anisotropic tissue in accordance with some examples of the present disclosure.

DETAILED DESCRIPTION

Figure 1:
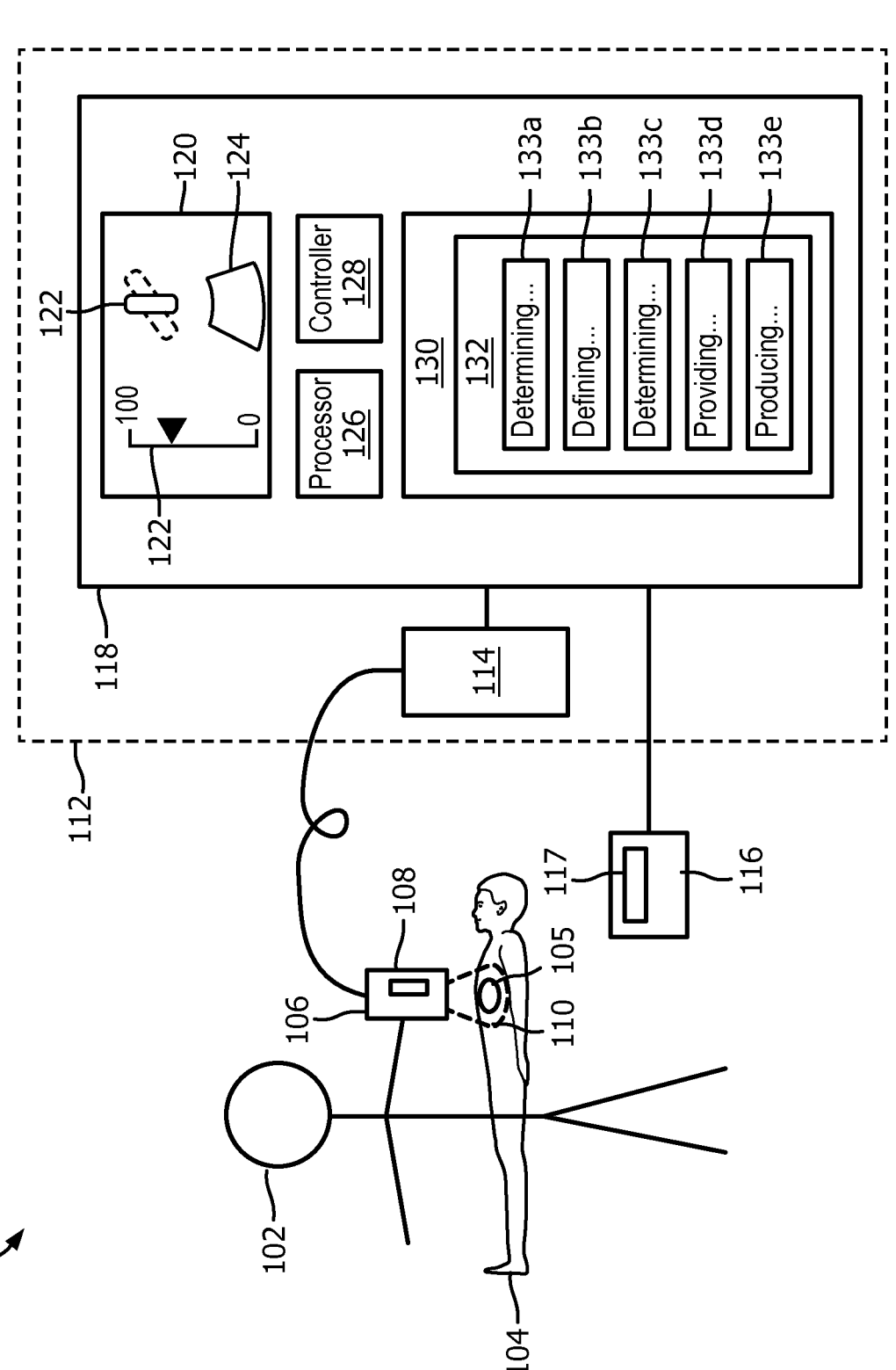
FIG. 1 is a block diagram of a system for guided shear wave elastography of anisotropic tissue constructed in accordance with some examples of the present disclosure.

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

The present technology is also described below with reference to block diagrams and/or flowchart illustrations of methods, apparatus (systems) and/or computer program products according to the present embodiments. It is understood that blocks of the block diagrams and/or flowchart illustrations, and combinations of blocks in the block diagrams and/or flowchart illustrations, may be implemented by computer executable instructions. These computer executable instructions may be provided to a processor, controller or controlling unit of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

Certain difficulties in the reliable acquisition of shear wave elastography images of anisotropic tissues at guided angles with respect to the tissues may be addressed by the examples herein, for example by providing feedback to the user (e.g., a sonographer) about the position and/or proximity of the probe's imaging plane to a desired or target imaging plane, and in some case by providing instructions to adjust a position of the probe and thus the corresponding imaging plane so as to position the probe to acquire a target view of the anisotropic tissue. Examples herein may, additionally or alternatively, enable collection of data at one or more target planes, increase the reliability of probe placement during such data collection, and/or allow accurate records of probe placement during measurement.

Various types of tissue may have anisotropic properties. For example, skeletal muscle exhibits anisotropic mechanical properties, i.e., tissue stiffness varies as function of the load direction. To fully characterize the stiffness of the muscle, multiple stiffness measurement points are typically required at different angles between the transducer imaging plane and muscle fiber orientation (for example, fibers in-plane and fibers cross-plane as the two extreme cases).

Recent research indicates more diagnostic potential by multidirectional stiffness measurement over the full range of the imaging angle. However, it can be challenging for sonographers to accurately maneuver the probe orientation and determine the angle between the imaging plane and muscle fiber direction. Ultrasound systems and methods for shear wave elastography in accordance with the present disclosure may facilitate the control of the shear wave imaging plane with respect to the fiber orientation, leading to more accurate assessment of muscle stiffness as function of load direction, which may enable more complete, accurate and standardized quantitative stiffness measurements for organs and tissues exhibiting anisotropic behavior. Although certain examples are described herein with respect to musculoskeletal tissue, it will be understood that the principles of the present disclosure can apply equally to any type of anisotropic tissue (e.g., vascular wall tissue, myocardium, and others).

The apparatus, system, and method in accordance with embodiments of the present disclosure are directed to guiding a position (e.g., location in space and angle) of a shear wave elastography imaging system with respect to the tissue. The imaging system may include a probe to send and receive ultrasound pulses in order to form an image of the tissue in an imaging plane. A position measurement system (e.g., a position tracking system) coupled to the probe may determine a position of the imaging plane with respect to the position measurement system coordinate system (world coordinate system) in real-time. Feedback about the position of the current imaging plane with respect to the world coordinate system may be provided to a user (e.g., via a graphic display) of the system to guide the placement of the imaging plane and capture data at a determined position. The system may guide the user to position and re-position the imaging plane (e.g., by repositioning or rotating a probe) at a variety of different positions about the tissue. By recording images of B-mode, shear wave elastography and/or other modalities at a plurality of positions, and recording the position each image was taken at, the system may build a more complete picture of properties of the anisotropic tissue.

FIG. 1 depicts an operational environment 100 associated with an ultrasound imaging system 112 according to some embodiments of the present disclosure. Components of the operational environment 100 may be used, at least in part, to implement embodiments of the present disclosure. For example, FIG. 1 shows an ultrasound imaging system 112, which may include or be operatively coupled to a probe 106, an ultrasound base 114 and a processing unit 118 (which may be within the base in some embodiments), a position tracking system 116, which may include or be operatively associated with a position field generator 117 and a sensor 108 attached to the probe 106, and a user 102 ultrasonically imaging a subject 104 with the probe 106. The components shown in FIG. 1 are merely illustrative, and other variations, including eliminating components, combining components, rearranging components, and substituting components are all contemplated.

In the operational environment 100 of FIG. 1, the user 102 may utilize the probe 106, which may be part of and/or communicatively connected to an ultrasound imaging system 112 to ultrasonically inspect anisotropic tissue 105 of the subject 104, and more specifically to obtain ultrasound shear wave elastography images of the anisotropic tissue 105 of the subject 104. The probe 106 may be arranged with respect to the anisotropic tissue 105 such that it scans a measurement plane 110, which includes a cross-section of the anisotropic tissue 105. The probe 106 may include the sensors 108, which may be coupled to the position measurement system 116 to determine a position (e.g., spatial location and/or orientation) of the probe 106 and thereby the position of the measurement plane 110. In one example, the sensors 108 may interact with an electromagnetic field generated by a field generator 117 of the position measurement system 116 to determine position of the sensors 108. In other examples, the position measurement system 116 may involve optical tracking (e.g., optical sensors recording a position of optical markers on the probe), mechanical tracking (e.g., attaching the probe to a robotic arm, a rigid stereotactic frame), and/or ultrasound image-based tracking. Other position measurement or tracking systems may be used in other embodiments. The probe 106 may be coupled to image data acquisition components, which may be located in an imaging base 114 of the ultrasound system 112 to acquire image data at the measurement plane 110.

The ultrasound system 112 includes an ultrasound base 114 coupled to the probe 106 and a processing unit 118. The processing unit 118 may receive data about the position of the probe 106 from the position tracking system 116 and/or sensors 108, and may receive measurement data from the ultrasound base 114. In some embodiments, the processing unit 118 may be a computer coupled to the ultrasound base 114. The ultrasound system 112 may include the display 120, the processor 126, the controller 128, and the memory 130 including the instructions 132 which may include one or more steps 133a-133e. The processor 126 and/or controller 128 may operate based on the instructions 132 to analyze information and/or control the ultrasound system 112. The display 120 may display at least one image 124 and/or one or more visual indicators 122 based on the measurement data from the ultrasound imaging system 112 and/or the position data from the sensors 108 and/or position tracking system 116.

The probe 106 may be used to image a region of interest in biological tissue, for example a region including anisotropic tissue 105. As described, anisotropic tissue is generally tissue that may have different properties, such as stiffness, depending on the orientation with respect to the tissue at which that property is being measured. In some examples, the anisotropic tissue 105 being imaged may be musculoskeletal tissue, myocardium tissue, vascular wall tissue, thyroid tissue, or any combination thereof. The examples herein may of course apply to other types of tissues than the specific examples described herein. One or more properties, such as stiffness, of the anisotropic tissue 105 may be measured and may be used to evaluate and/or diagnose conditions such as injury, dystrophy, and/or myositis.

The probe 106 may be used to acquire a shear wave elastography image(s) of the anisotropic tissue 105. To that end, the probe 106 may include a transducer which is operable to transmit a "push pulse" toward the anisotropic tissue 105, generating a shear wave which then propagates through the anisotropic tissue 105. Alternatively, the shear wave in the tissue may be generated without acoustic radiation force but via mechanical force applied externally to the tissue, such as by a mechanical vibrator configured to compress the tissue. The probe 106 may be further operable to emit tracking pulses, which may be used to measure the velocity of the shear wave as it propagates. The measured velocity of the shear wave may be analyzed (such as by processor 126) to determine a stiffness of the anisotropic tissue 105. The shear wave elastography data may be used to produce a shear wave elastography image.

The transducer of the probe 106 may be a linear (or one dimensional) transducer, which is operable to receive data generally from a single imaging plane 110. In some embodiments, the linear probe may be phased or steerable in the azimuth direction for an increased field of view. Nonetheless, a linear transducer may need to be physically repositioned (e.g., tilted or toe-heeled, or rotated to a different orientation with respect to the subject) in order to acquire image data in an elevationally different imaging plane through the biological tissue. When imaging a subject with a system according to the examples herein, the system may receive position data that specifies the position of the probe 106, including the spatial location (in 3D) of the probe and the orientation of the probe and thus imaging plane with respect to a reference frame (e.g., a coordinate system of the position measurement system). As the exam progresses, e.g., in order to acquire images at different orientations with respect to the tissue 105, the ultrasound system 112 may direct the user 102 to change a position of the probe 106 thereby changing the orientation of the imaging plane 110.

The probe 106 may be coupled to position tracking system 116 to determine a position of the probe 106 with respect to the position tracking system 116. The probe 106 may include at least one sensor 108, which may receive information from the position tracking system 116. The at least one sensor 108 may be attached to the probe 106 or may be integral to the probe 106. The position tracking system may have a known spatial relationship with the subject 104. In some examples, the position tracking system may be registered to the subject 104, e.g., by spatially registering the probe 106 to the subject such as at the start of the ultrasound exam. As illustrated, the position tracking system 116 may include a position field generator 117 which produces a field that interacts with the at least one sensor 108. In one embodiment, the at least one sensor 108 may measure a property of the field. In another embodiment, the at least one sensor may create a disturbance in the field that may be measured by the position field generator 117.

The measurements from the at least one sensor 108 and/or position field generator 117 may be used to determine the position of each of the at least one sensors 108 with respect to the position field generator 117. These measurements may in turn be used to determine a position of the probe 106 based on known relationships between the positions of each of the at least one sensors 108 and the probe 106. The measurements may be transmitted to the ultrasound system 112 for determination of the position of the probe 106, or these calculations may be made by a processor located in the position tracking system 116 or in the probe 106. Although FIG. 1 depicts the position tracking system 116 as being coupled to the ultrasound system 112, in some embodiments, the position tracking system 116 has no direct connection to the ultrasound system 112 and the sensors 108 of the probe 106 provide the position measurements to the ultrasound system 112. The sensors 108 may be directly coupled to the ultrasound system 112 or may be indirectly coupled via the probe 106 and/or position tracking system 116.

As described in greater detail herein, the position tracking system 116 may have a known relationship with a position of the subject 104 and/or anisotropic tissue 105, allowing a relationship between a position of the probe 106 and the position of the anisotropic tissue 105 to be determined. In an example, the position field generator 117 may be located underneath the subject 104, such as embedded in a mattress supporting the subject 104. In other examples, the relationship between the probe 106 and the anisotropic tissue 105 may not need to be determined, if it is assumed that the tissue 105 is not moving with respect to the position measurement system 116.

The position tracking system 116 may have a coverage zone about the subject 104 and/or anisotropic tissue 105. The coverage zone may define a region within which the location of the probe 106 can be determined. The size and shape of the coverage zone may be determined by properties of the position field generator 117. The coverage zone may be defined by moving the probe 106 and marking different locations. As an example, the ultrasound system 112 may prompt the user 102 (e.g., via the display 120) to move the probe 106 to one or more set locations in relation to the subject 104. The locations may be edges of an expected coverage zone. The ultrasound system 112 may register a size of the expected coverage zone and may subsequently provide feedback (e.g., via a tone and/or display 120) to indicate that the probe 106 is at or near an edge of the coverage zone.

In some embodiments, the position tracking system 116 may be an electromagnetic tracking system. The position field generator 117 may be an electromagnetic field generator, which generates an electromagnetic field about the subject 104. The sensors 108 may be electromagnetic sensors, which detect properties of the electromagnetic field (e.g., amplitude) at the location of the sensor 108. The electromagnetic field generator may be a tabletop electromagnetic generator and may be positioned on or near a structure (e.g., gurney, imaging table, bed) supporting the subject 104. Other forms of position tracking system 116 and sensors 108 may be used in other embodiments.

In the example in FIG. 1, the ultrasound system 112 is communicatively coupled to the probe 106 and the position tracking system 116. The ultrasound system 112 may receive data from the probe 106 and the position tracking system 116 and/or may control them to alter the operation of these components. The ultrasound system 112 may be provided as a mobile unit, such as on a cart, or as a portable handheld unit, such as a tablet. The probe 106 and/or position tracking system may be coupled to the ultrasound system 112 by a wired and/or wireless (e.g., Wi-Fi, Bluetooth) connection. The ultrasound system 112 may have an ultrasound base 114 coupled to the probe 106. The ultrasound base 114 may control the shear wave elastography sent by the transducer and receive data from the probe 106. Although FIG. 1 depicts the ultrasound base 114 and the processing unit 118 as separate components of the ultrasound system 112, it is to be understood that the ultrasound base 114 may share components with the processing unit 118, such as processor 126, controller 128, and memory 130. In some embodiments, the ultrasound base 114 and the processing unit 118 may be integrated into a single unit.

The ultrasound system 112 includes the operation unit 118, which is coupled to the probe 106 (via the ultrasound base 114) and the position tracking system 116. The operation unit 118 may receive shear wave elastography data from the probe 106 (and/or ultrasound base 114) and generate one or more shear wave elastography images 124. The processor 126 may utilize the instructions 132 (e.g., by executing step 133a) to analyze data from the probe 106, sensors 108, and/or position tracking system 116 to determine the position of the probe 106. The position of the probe 106 may be determined in real-time. The position and/or images 124 may additionally be stored in memory 130. The processor 126 may determine one or more target locations or planes at which images are to be taken (e.g., by executing step 133b of instructions 132) and determine a difference between the current position of the probe 106 and the target plane (e.g., by executing step 133c). The processor 126 may operate the instructions 132 to generate one or more visual indicators

122, which depict a current position of the imaging plane 110 with respect to a target plane of the anisotropic tissue 105 (e.g., by executing step 133d). The processor 126 may execute the instructions 132 to produce a shear wave image when the probe 106 and the target plane are aligned (e.g., step 133e). The processing unit 118 may include a display 120, which displays the images 124 and/or the visual indicators 122. Although certain specific steps 133a-133e of the instructions 132 have been described, it is to be understood, that the instructions 132 may include more or less steps, and that steps may be repeated, rearranged, and/or selectively changed.

The processor 126 may generate one or more visual indicators 122, which may guide positioning of the probe 106 such that the position of the imaging plane 110 matches a position of a target plane. The visual indicators 122 may provide feedback to a user 102 to manually adjust a location of the imaging plane 110 by moving the probe 106. The processor 126 may directly adjust the position of the probe 106 and/or imaging plane 110 by generating instructions to update the position of the probe 106 and/or imaging plane 110 and controlling actuators with the controller 128 based on those instructions to adjust the position of the probe 106 and/or imaging plane 110 to match the position of a target plane. The ultrasound system 112 may generate a variety of target planes to guide shear wave elastography imaging of the anisotropic tissue 105 at a variety of positions with respect to the anisotropic tissue 105. The visual indicators 122 may increase an accuracy of probe 106 positioning at each of the variety of positions.

The ultrasound system 112 may capture shear wave elastography images (data) along the imaging plane 110, and may also store and/or retrieve previously recorded data for later review. The images 124 and/or position data may be saved in memory 130 and recalled as needed. The ultrasound system 112 may categorize different images based on specific positions at which data was collected, and may allow a user 102 to sort or select different images based on these categorizations. For example, the ultrasound system 112 may have a 'Find Orthogonal' tool which selects the image which is orthogonal to a currently displayed image. Reports may be generated based on selections of the saved data in the memory 130.

Figure 2:
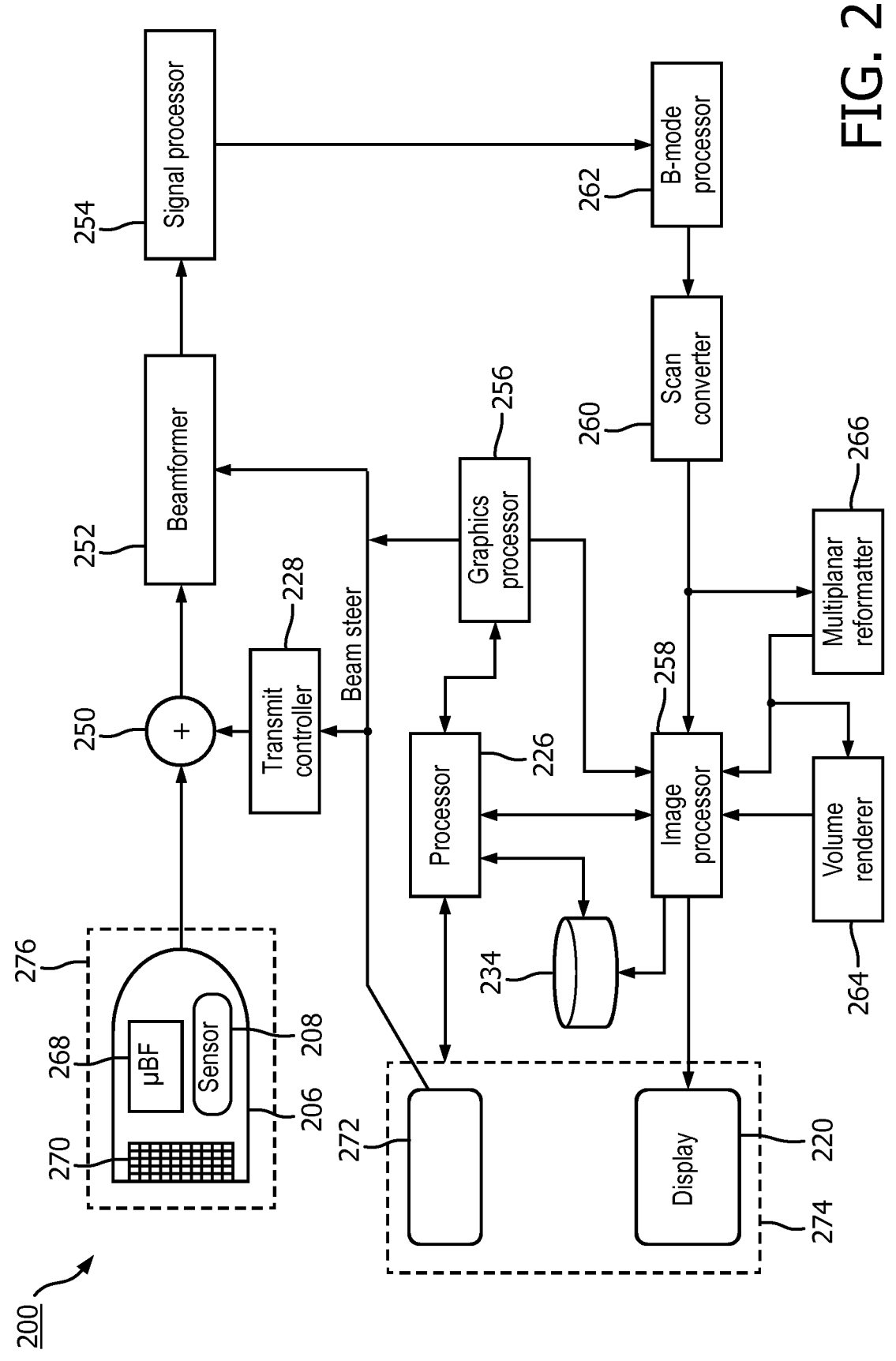
FIG. 2 is a block diagram of an ultrasound system in accordance with some examples of the present disclosure.

FIG. 2 shows a block diagram of an ultrasound imaging system 200 according to some embodiments of the present disclosure. The ultrasound imaging system 200 may be used to implement, at least in part, the ultrasound system 112 of FIG. 1. FIG. 2 shows an ultrasound imaging system 200, which includes ultrasound probe 206, transducer array 270, microbeamformer 268, transmit/receive (T/R) switch 250, beamformer 252, transmit controller 210, signal processor 254, B-mode processor 262, scan converter 260, multiplanar reformatter 266, volume renderer 264, image processor 258, graphics processor 256, user interface 274, input device 272, and output device 220. The components shown in FIG. 2 are merely illustrative, and other variations, including eliminating components, combining components, rearranging components, and substituting components are all contemplated.

The ultrasound imaging system 200 includes a probe 206, which may be used to implement the probe 106 of FIG. 1 in some embodiments. The probe 206 is positioned about a subject and used to capture data about tissues of the subject. In the ultrasound imaging system 200 in FIG. 2, the ultrasound probe 206 includes a transducer array 270 for transmitting ultrasonic waves and receiving echo information. A variety of transducer arrays are well known in the art, e.g., linear arrays, convex arrays or phased arrays. The transducer array 270 for example, can include a two dimensional array of transducer elements capable of scanning in both elevation and azimuth dimensions for 2D and/or 3D imaging. The transducer array 270 is coupled to a microbeamformer 268, typically located in the ultrasound probe 206, which controls transmission and reception of signals by the transducer elements in the array. In this example, the microbeamformer 268 is coupled, such as by a probe cable or wirelessly, to a transmit/receive T/R switch 250, which switches between transmission and reception. The T/R switch 250 may thus protect the beamformer 252 from high energy transmit signals. In some embodiments, the T/R switch 250 and other elements of the system can be included in the transducer probe rather than in a separate ultrasound system base (e.g., ultrasound base 114).

The transmission of ultrasonic beams from the transducer array 270 under control of the microbeamformer 268 is directed by the transmit controller 228 coupled to the T/R switch 250 and the beamformer 252. The transmit controller 228 receives input from the user's operation of an input device 272 of user interface 274. The transmit controller 228, may be a component of an ultrasound system base (e.g., ultrasound base 114 of FIG. 1), or may be a general controller of the ultrasound system (e.g., controller 128 of FIG. 1). The user interface 274 may be implemented using one or more input, such as control panels, which may include soft and/or hard controls, and output devices, such as one or more displays, as described further below. One of the functions controlled by the transmit controller 228 is the direction in which beams are steered. Beams may be steered straight ahead from (orthogonal to) the transducer array, or at different angles for a wider field of view. The partially beamformed signals produced by the microbeamformer 268 are coupled to a beamformer 252 where partially beamformed signals from individual patches of transducer elements are combined into a fully beamformed signal. The transmit controller 228 may record a position of the beams with respect to the probe 206. As described here, the position of the beams and the probe 206 may be used to determine a position of an imaging plane (e.g., imaging plane 110 of FIG. 1).

The beamformed signals may be coupled to a signal processor 254. The signal processor 254 can process the received echo signals in various ways, such as bandpass filtering, decimation, I and Q component separation, and harmonic signal separation. The signal processor 254 may also perform additional signal enhancement such as speckle reduction, signal compounding, and noise elimination. The processed signals may be coupled to a B-mode processor 262, which can employ amplitude detection for the imaging of structures in the body. The signals produced by the B-mode processor may be coupled to a scan converter 260 and a multiplanar reformatter 266. The scan converter 260 arranges the echo signals in the spatial relationship from which they were received in a desired image format. For instance, the scan converter 260 may arrange the echo signal into a two dimensional (2D) sector-shaped format, or a pyramidal three dimensional (3D) image. The multiplanar reformatter 266 can convert echoes, which are received from points in a common plane in a volumetric region of the body into an ultrasonic image of that plane, as described in U.S. Pat. No. 6,443,896 (Detmer). A volume renderer 264 converts the echo signals of a 3D data set into a projected 3D image as viewed from a given reference point, e.g., as described in U.S. Pat. No. 6,530,885 (Entrekin et al.) The 2D or 3D images may be coupled from the scan converter 260, multiplanar reformatter 266, and volume renderer 264 to an image processor 258 for further enhancement, buffering and temporary storage for display on an output device 220. The output device 220 may include a display device implemented using a variety of known display technologies, such as LCD, LED, OLED, or plasma display technology. In some embodiments, the output device 220 may implement the display 120 of FIG. 1.

The graphics processor 256 can generate graphic overlays for display with the ultrasound images. These graphic overlays can contain, e.g., standard identifying information such as patient name, date and time of the image, imaging parameters, and the like. The graphics processor may receive input, such as a typed patient name, from the input device 272. The input device 272 may include one or more mechanical controls, such as buttons, dials, a trackball, a physical keyboard, and others, which may also be referred to herein as hard controls. Alternatively or additionally, the input device 272 may include one or more soft controls, such as buttons, menus, soft keyboard, and other user interface control elements implemented for example using touch-sensitive technology (e.g., resistive, capacitive, or optical touch screens). To that end, the ultrasound imaging system 200 may include a user interface processor (i.e., processor 226), which may control operations of the user interface such as functions associated with soft controls. One or more of the user controls may be co-located on a control panel. For example, one or more of the mechanical controls may be provided on a console and/or one or more soft controls may be co-located on a touch screen, which may be attached to or integral with the console. For example, in some embodiments the input device 272 may be part of the processing unit 118 and/or ultrasound base 114 of FIG. 1.

The ultrasound images and associated graphics overlays may be stored in memory 230, for example for off-line analysis. In addition, the memory 230 may store processor-executable instructions including instructions for performing functions associated with the user interface 274. In some embodiments, the user interface 274 may include a graphical user interface, which may be configured to display, responsive to a processor of the system 200, graphical user interface elements for providing guidance to the sonographer in performing shear wave elastography of anisotropic tissue in accordance with any of the examples herein. The memory 230 may be a part of an ultrasound base unit, or may be a general memory that is part of a computer system coupled to the base unit (e.g., the memory 230 may be memory 130 of processing unit 118 of FIG. 1). The user interface 274 can also be coupled to the multiplanar reformatter 266 for selection and control of a display of multiple multiplanar reformatted (MPR) images. In some examples, functionality of two or more of the processing components (e.g., beamformer 252, signal processor 254, B-mode processor 262, scan converter 260, multiplanar reformatter 266, volume renderer 264, image processor 258, graphics processor 256, processor 226, etc.) may be combined into a single processing unit such as processor 126 of FIG. 1.

The probe 206, sensor 208, microbeamformer 268, and transducer 270 may be combined into a handheld unit 276. The handheld unit 276 may be shaped to be held in a user's hand. The handheld unit 276 may have a 'head' or 'face' containing the transducer 270 and shaped to be positioned on a surface of a subject (e.g., against the skin). The sensor 208 may, in some embodiments, implement the at least one sensor 108 of FIG. 1. Although only a single sensor 208 is show in FIG. 2, it is to be understood that the sensor 208 may represent a plurality of sensors positioned about the probe 206. The sensor 208 may be integral, such as contained within a housing of the probe 206, may be a separate component attached to an outside of a housing of the probe 206, or may be a combination of integral and combined. The sensor 208 may be located in a fixed position relative to the probe 206, so that by knowing a position of the sensor 208, a position of the probe 206 and imaging plane is also known.

Figure 3B:
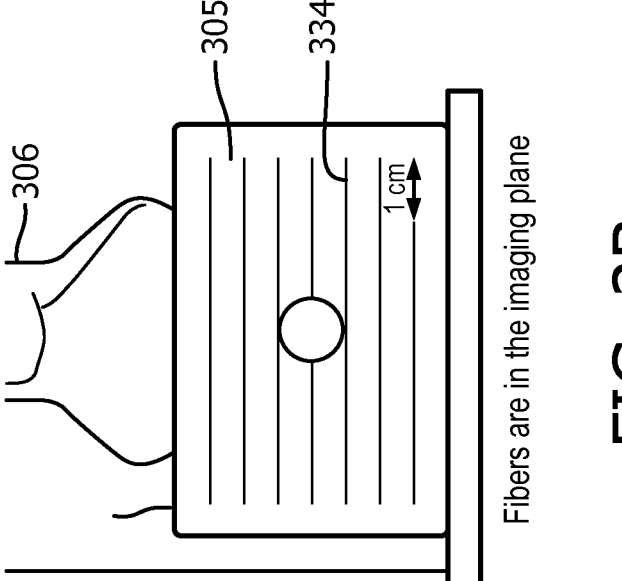
FIGS. 3A, 3B, 3C, 3D, 3E and 3F are illustrations of probe placement with respect to anisotropic tissue in accordance with some examples of the present disclosure.
Figure 3A:
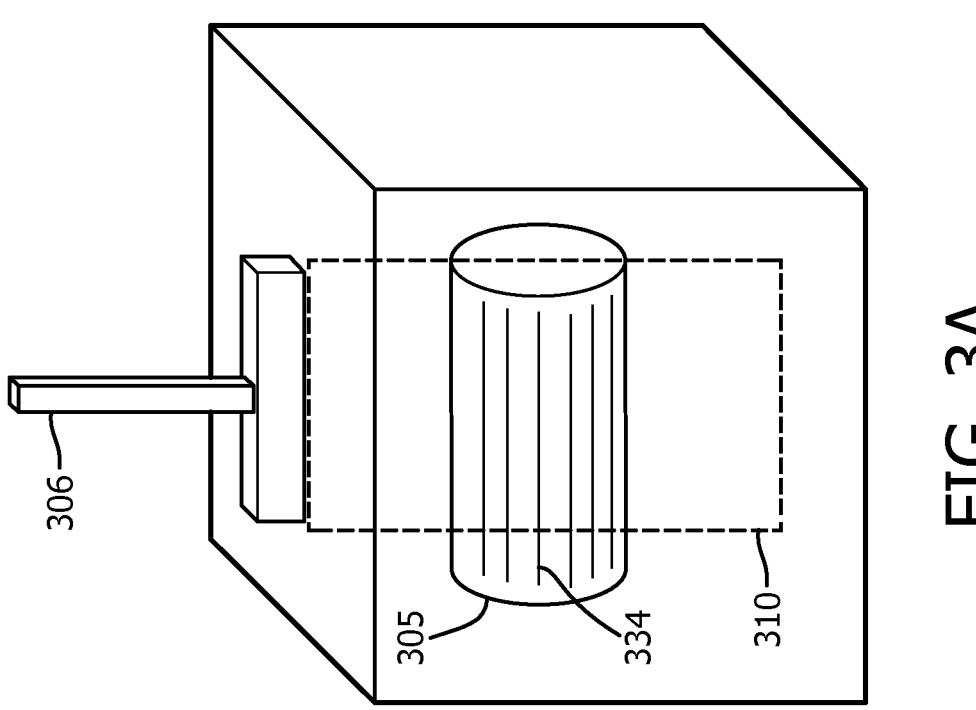
Figure 3D:
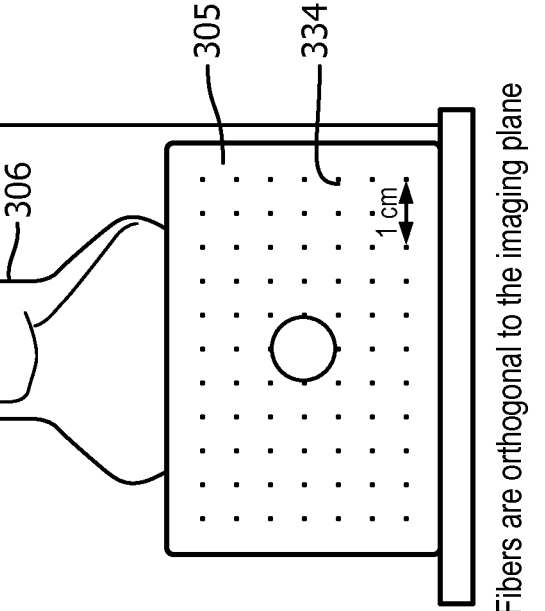
Figure 3C:
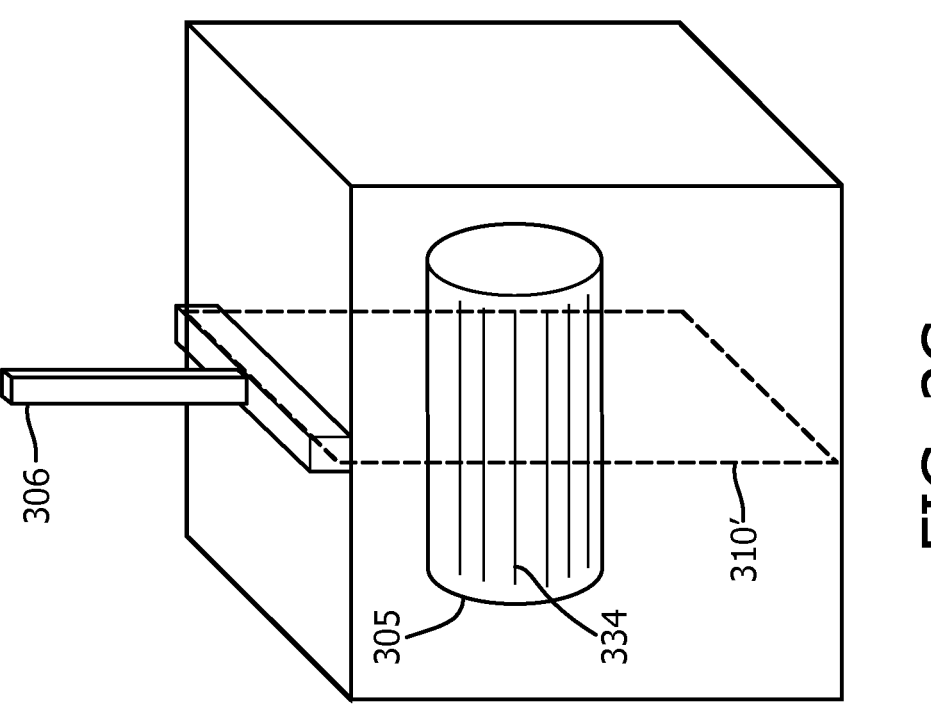
Figure 3E:
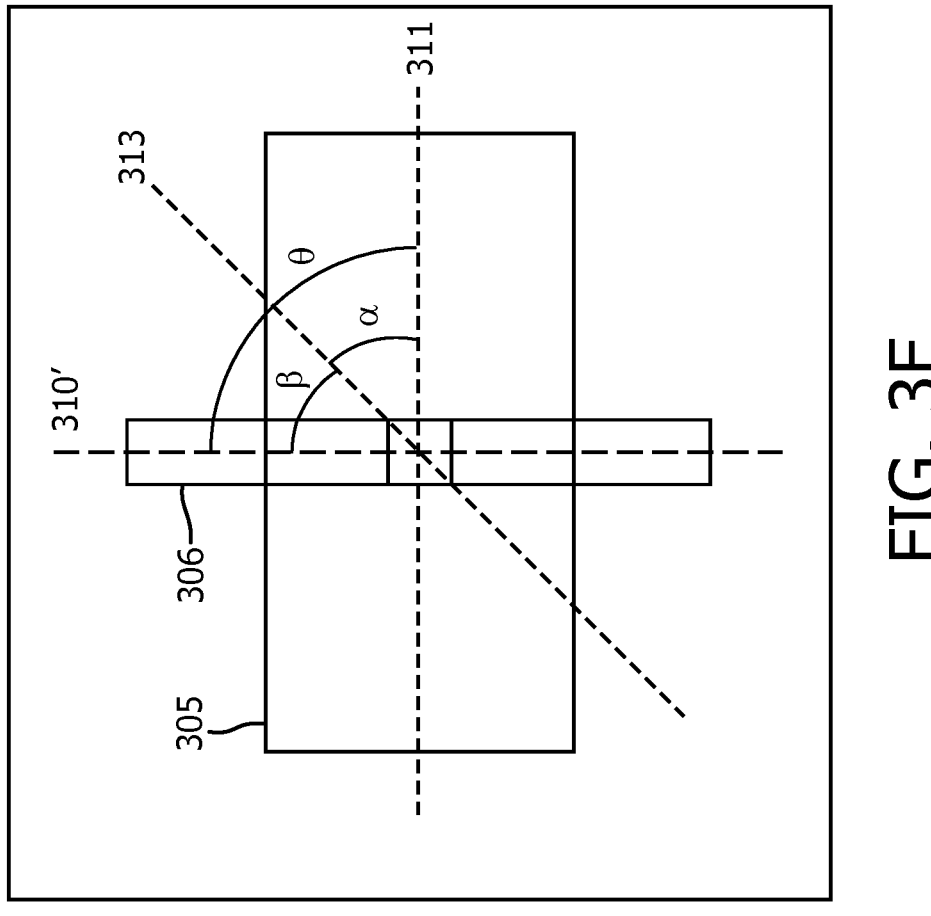
Figure 3F:
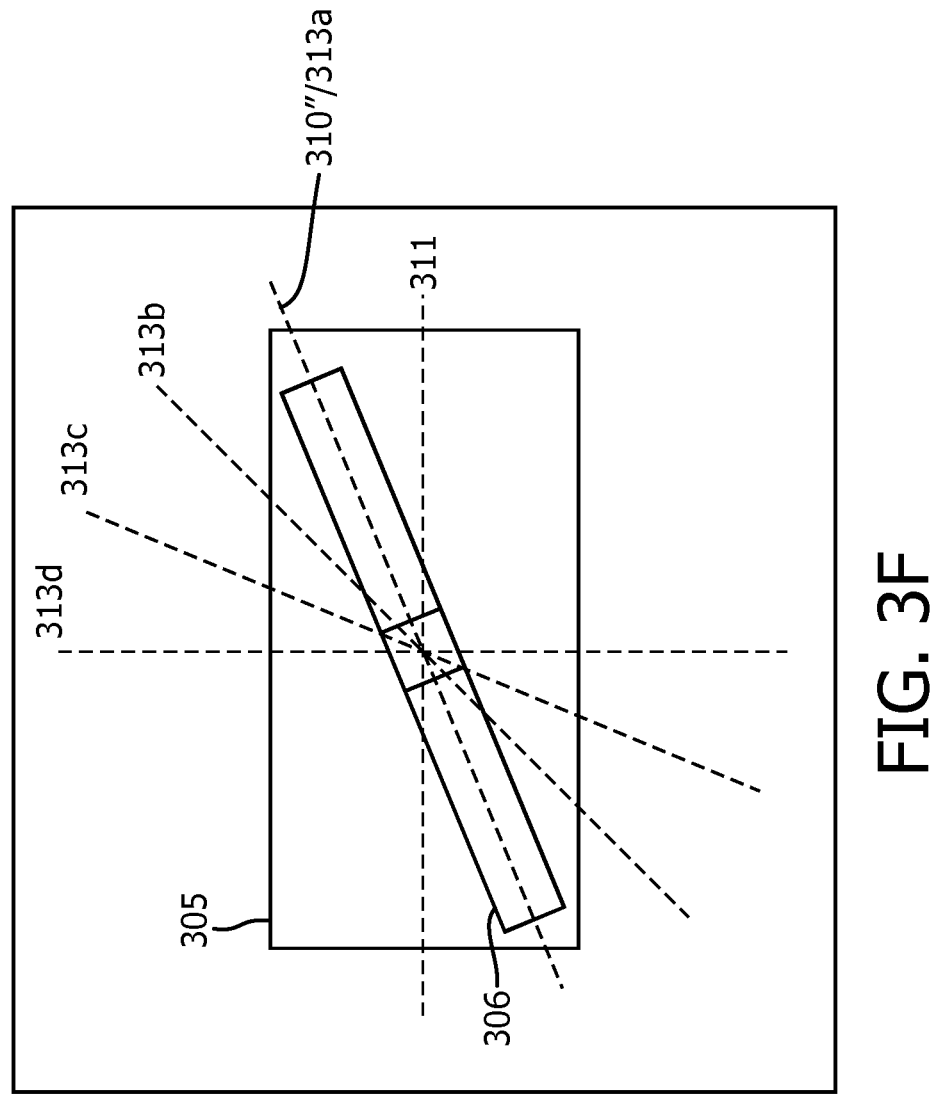

FIGS. 3A-3F illustrate probe placement with respect to anisotropic tissue in accordance with examples the present disclosure. The placement of the probe may be defined by the position of planes intersecting the tissue. The relationships between these planes may be determined and may be used to guide placement of the probe during one or more imaging operations. FIGS. 3A-3D depict anisotropic tissue 305, fibers 334, probe 306, imaging plane 310, rotated imaging planes 310' and 310", reference plane 311, and at least one target plane 313 and 313a-313d. FIGS. 3A and 3C depict a probe placed in two different positions with respect to anisotropic tissue. FIGS. 3B and 3D depict imaging planes through the tissue captured by the probe at the positions of FIGS. 3A and 3C respectively. FIG. 3E is a top down view of the tissue depicting a target plane 313. FIG. 3F is a top down view similar to 3E, except that there are multiple imaging planes 313a-313d. The examples shown in FIGS. 3A-3F are merely illustrative, and other variations, including eliminating components, combining components, rearranging components, and substituting components are all contemplated.

The probe 306 may be an implementation of the probe 106 of FIG. 1 in some embodiments. The probe 306 may be positioned against a surface of the subject (e.g. on the skin) proximate a region of anisotropic tissue 305. The anisotropic tissue 305 may include fibers 334, the orientation of which may at least partially determine the anisotropic properties of the anisotropic tissue 305. That is, a given property, such as stiffness, of the tissue 305 when measured with the imaging plane of the probe 306 aligned with the direction of the fibers of the tissue 305 may be different from the given property (e.g., stiffness) when measured with the imaging plane of the probe 306 not aligned with the direction of the fibers. The probe 306 collects data from an imaging plane 310, which may include a section of the anisotropic tissue 305. A reference plane 311 may be defined in the tissue, and an angle θ measured between the current position of the imaging plane 310 and the position of the reference plane 311. One or more target planes 313, 313a-d may also be defined in the anisotropic tissue 305, which may have an angle α with respect to the reference plane and an angle β with respect to the current imaging plane 310.

FIG. 3A depicts a probe 306 being used for shear wave elastography imaging of a region of anisotropic tissue 305. The anisotropic tissue 305 may include fibers 334. The fibers 334 may be generally aligned. The fibers 334 may have different mechanical properties measured across the fiber than the same property measured along the fiber. In some instances, the orientation of the fibers 334 may define the anisotropic properties of the anisotropic tissue 305. The fibers 334 may be, for example, muscle fibers. The probe 306 may collect data from an imaging plane 310 extending through the tissue.

FIG. 3B shows a cross sectional view of the anisotropic tissue 305 corresponding to the imaging plane 310. In this example, the imaging plane is shown as being generally aligned along a long axis of the fibers 334. The fibers 334 run across the imaging plane 310. The imaging plane 310 is depicted as being generally rectangular, however other shapes of the imaging plane 310, such as curvilinear, trapezoidal, sector, and/or radial, may be used in other examples.

FIGS. 3C and 3D are similar to FIGS. 3A-B respectively, except that probe 306 has changed position relative to its positioning in FIGS. 3A-B and is now collecting data from image plane 310'. In FIGS. 3C and 3D, the imaging plane 310' is shown as generally aligned across the long axis of the fibers 334 (e.g. rotated about 90° from FIGS. 3A-B). The image of FIG. 3D shows the fibers 334 running in and out of the imaging plane 310'.

FIGS. 3E and 3F depict a simplified top-down view of the probe 306 and anisotropic tissue 305. For reference, the anisotropic tissue 305 is shown in the top down view, even though it may be obscured from view (e.g., under the skin). The fibers of the anisotropic tissue 305 have been omitted from these Figures for clarity, although it is to be understood that the anisotropic tissue 305 may still have fibers, which for example, may run from left to right in this view. A reference plane 311 may be defined relative to the anisotropic tissue 305 such that the position of the imaging plane 310 may be described in relationship to the position of the reference plane 311. In this example, the reference plane 311 is defined as the plane aligned with the long axis of the fibers 334 (e.g., the position of the imaging plane 310 in FIGS. 3A-3B). Since the position of the probe 306 is rotated with respect to the position of the reference plane, the position of the case image plane 310' may be measured as an angle θ between the reference plane 311 and the image plane 310'. In the case of FIGS. 3E, the angle θ may be about 90°.

In some embodiments, the reference plane 311 may be defined in relation to one or more features of the anisotropic tissue 305. The reference plane 311 may align with known anatomical structures (e.g., along a long axis of a bone or along an expected direction of muscle fibers). The reference plane 311 may be aligned with features of the anisotropic tissue 305. The reference plane 311 may, for example, be aligned with a long axis of fibers of muscle tissue. The system (e.g. ultrasound system 112 of FIG. 1) may be used to determine the location of the reference plane 311. In an example, a 3D scan of anisotropic tissue 305 may be performed, and anatomical features may be identified by the system (e.g., with processor 126 of FIG. 1) with techniques such as by machine learning. The system may then define the reference plane 311 based on the identified anatomical features. In one embodiment, the system may estimate a direction of fibers in the anisotropic tissue 305 based on the 3D scan, and align the reference plane 311 with an estimated long axis of the fibers. Other methods of defining the reference plane 311 may be used in other examples.

In some embodiments, the reference plane 311 may be selected by a user (such as user 102 of FIG. 1). The probe 306 may include a reference frame selector (e.g., a button). When the reference frame selector is activated, an ultrasound system (e.g., ultrasound system 112 of FIG. 1) may record the current position of the imaging plane 310 as the reference plane 311. In the example of FIGS. 3A-F, for example, the reference frame selector may have been activated while the probe 306 was in the position of FIGS. 3A-3B. Other methods of user selection of the reference plane 311 may be used in other embodiments.

A system (e.g., ultrasound system 112 of FIG. 1) may be used to save images taken along the image plane 310', 310", along with position information for each of the images defined with respect to a reference plane 311 (e.g., each image may be associated with an angle θ). The system may include a 'Recalibrate reference plane' tool. The system may selectively allow a new reference plane to be chosen for the saved images. The new reference plane may be selected from one of the saved images, and may be selected by a user of the system. The system may update the position data saved with the images (e.g., by overwriting the old position data) to reflect the position of the image with respect to the new reference plane. The 'recalibrate reference plane' tool may be used to account for changes in measurement position over time, for example if the probe 306 is moved over the course of a measurement sequence.

FIGS. 3E and 3F show further examples of positioning of the probe 306 with respect to target plane 313 (in FIG. 3E), or with respect to any one of a plurality of target planes in FIG. 3F). The target planes 313, 313a-d may represent positions (or imaging planes) at which it may be desirable to acquire a shear wave elastography image. As such an indicator of a target plane 313 may represent a position at which the imaging plane 310' of the probe 306 should be aligned in order to acquire images at the desired imaging planes. An ultrasound system (such as ultrasound system 112 of FIG. 1) may generate operator guidance (e.g., graphical user elements providing indicators for one or more target planes) to assist the user in acquiring the appropriate image data. The target planes 313, 313a-d may have a pre-determined position with relationship to the reference plane 311. In some examples, target plane 313 may be defined (e.g., by the system and/or responsive to user inputs) at pre-determined angle(s) with respect to the reference plane 311. A plurality of target planes 313a-d may be defined at set angular intervals from the reference plane. In one example, a plurality of target planes are defined at 150 angular intervals such that a first target plane is defined at 150 with respect to the reference plane and additional target planes are defined at 150 angular increments from the preceding target plane. Other angular intervals (e.g., 5°, 10°, 20°, 25°, etc.) may be used in other examples, and the angular intervals and ranges may be selected by the user of the system. In some examples, the system may be preset to define target planes at given angular intervals, and the presets may in some cases be adjustable by the user.

The position of each of the target planes 313, 313a-d may be described in relation to the reference plane 311. In the example of FIG. 3E as shown, where the planes are all rotated about an axis, an angle $\alpha$ may exist between the reference plane 311 position and the target plane 313 position. An angle $\beta$ may exist between the current imaging plane 310 and the target plane 313. Similar to FIGS. 3A-3D, the reference plane 311 is chosen to align with a long axis of the fibers 334 of the anisotropic tissue 305. The target plane 313 has been selected to lie about 45° (counter-clockwise) from the reference plane 311. Accordingly, in this example, angle $\alpha$ may be about 45°. Other angles and locations of target planes may be used in other examples.

The position of the imaging plane 310 may be adjusted to match a position of the target plane 313. This may take the form of reducing the angle $\beta$ until it is about 0°, or within a threshold value of 0°. A shear wave elastography image may be produced when the imaging plane 310 is aligned with the location of a target plane 313. A shear wave elastography image may be recorded when the imaging plane 310 is close to the target plane 313 (e.g., the angle $\beta$ is below a chosen threshold). The shear wave elastography images may be recorded automatically by a system (such as ultrasound system 112 of FIG. 1) or when selected by a user. The current angle $\theta$ may also be recorded along with the shear wave elastography image. As shown in the example FIGS. 3E, the image plane 310' is currently located at an angle $\theta$ of about 90° with respect to the reference plane 311. The current position of the imaging plane 310' may match the location of a previous target plane. The imaging plane

310' may need to be rotated through about −45° (e.g., a clockwise rotation of 45°) to align with the location of the target plane 313. Although only one target plane 313 and one rotation is shown in this example, the position of the imaging plane 310 may be rotated again to match a next target plane. Other rotations and target plane locations are used in other examples.

FIG. 3F is similar to FIG. 3E, except that in the embodiment of FIG. 3F, a plurality of target planes 313a-313d have been generated by the system, and the probe 306 is rotated such that the imaging plane 310'' has a different position than the imaging planes 310 and 310' of FIGS. 3A-3E. In FIG. 3F, similar to FIG. 3A-3E, a reference plane 311 has been defined which lines along an axis of fibers of the anisotropic tissue 305. The ultrasound imaging system may generate a plurality of target planes 313a-d, and then generate instructions to position the imaging plane 310 for alignment with each of the plurality of target planes 313a-d in a sequence. The system may order the target planes 313a-d of the sequence to minimize movement of the probe 306 between each alignment of the sequence. In the example shown in FIG. 3F, the ultrasound system (e.g., ultrasound system 112 of FIG. 1) has produced four target planes 313a-d in relation to the reference plane 311. Each of the target planes 313a-313d is spaced at an angular interval of about 22.5°. Thus, measuring clockwise from the reference plane 311, target plane 313a is at about 22.5°, target plane 313b is at about 45°, target plane 313c is at about 67.5°, and target plane 313d is at about 90°. Although the target planes 313a-d have been shown at regular rotational intervals, it is to be understood that target planes may be generated based on a variety of criteria. In some examples, the target planes may be irregularly spaced. In some examples, additional positional changes beyond rotation may be indicated. Similarly, although only four target planes 313a-d are shown in this example, it should be understood that the system may produce more or less target planes.

As shown in FIG. 3F, the probe has been rotated so that the current imaging plane 310'' is aligned with the first target plane 313a. Once the system (e.g., ultrasound system 112 of FIG. 1) records an image at this position (either automatically, or after prompting a user to save the image), the system may update to produce directions to position the probe 306 in alignment with the next target plane 313b. Thus, the system may produce instructions which indicate that the probe 306 should be rotated by 22.5° from the position of the current imaging plane 310'' to the position of target plane 313b. This process may repeat after an image is taken at each of the target planes 313a-d until the system indicates that there are no remaining target planes.

Figures 4A, 4B:
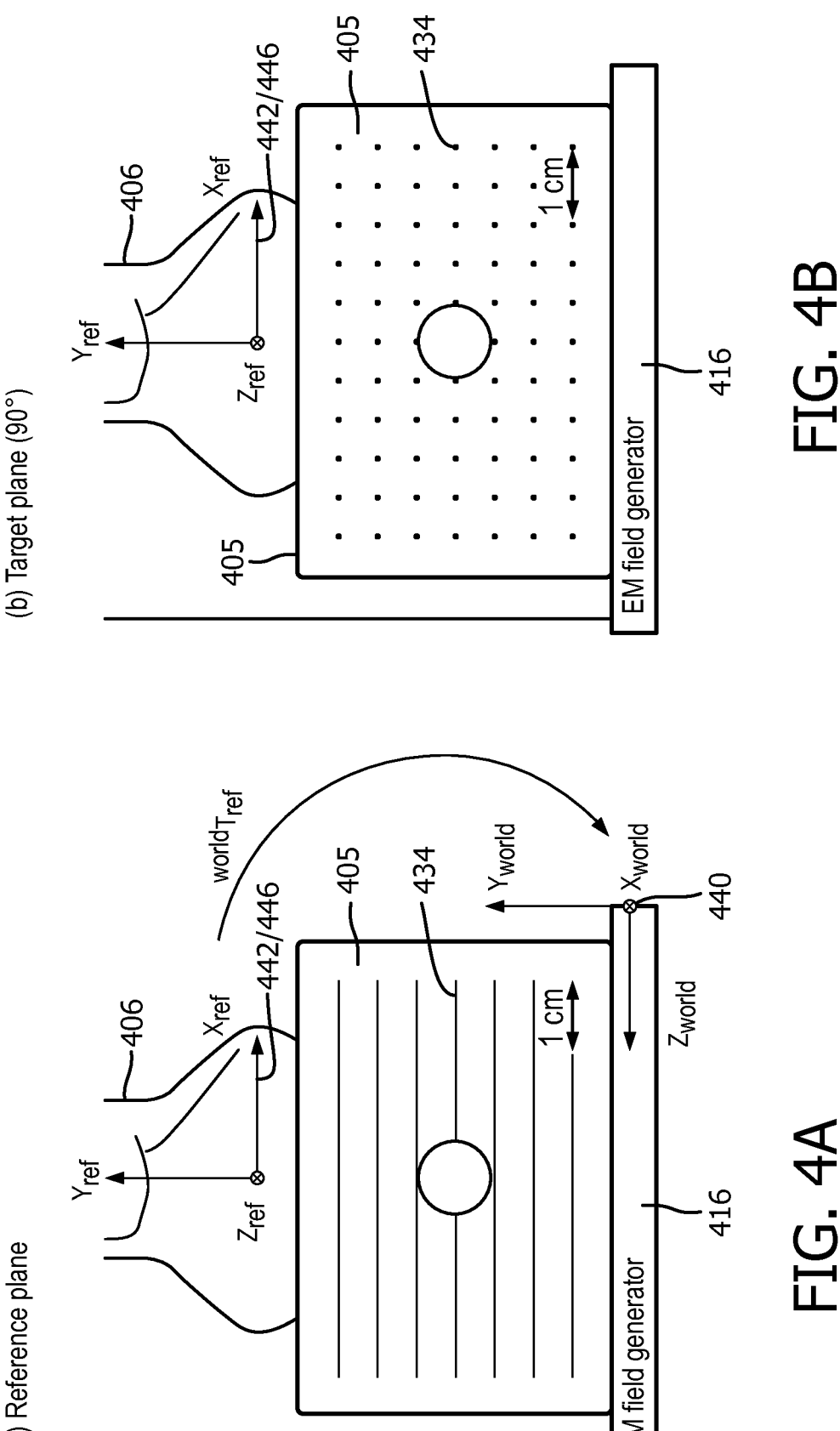
FIGS. 4A and 4B are illustrations of coordinate systems associated with components of exemplary systems, such as the probe and/or electromagnetic field generator in accordance with some examples of the present disclosure.

FIGS. 4A-4B illustrates further aspects of the present disclosure, and more specifically coordinate systems associated with the probe and/or other components of the system. FIGS. 4A-B show a probe 406, anisotropic tissue 405, fibers 434, position tracking system 416, position coordinate system 440, reference coordinate system 442, target coordinate system 444, and current coordinate system 446. The probe 406 may be an implementation of the probe 106 of FIG. 1 in certain embodiments. The examples shown in FIGS. 4A-4B are merely illustrative, and other variations, including eliminating components, combining components, rearranging components, and substituting components are all contemplated.

The coordinate systems illustrated in FIGS. 4A-4B may be defined and used by an ultrasound system (e.g., by the processor 126 of ultrasound system 112) to determine a difference between a current position of an imaging plane and a position of a target plane, and to generate instructions to adjust the position of the imaging plane to the position of the target plane. The coordinate systems may be used to determine positions and directions for changing those positions in up to three spatial and three rotational dimensions. FIG. 4A shows probe 406 aligned along a reference plane, which may be aligned along a long axis of fibers 434 running through anisotropic tissue 405. For clarity, the probe 406 is depicted as positioned directly on anisotropic tissue 405, however it is to be understood that there may be one or more additional tissues (e.g., fat, skin) of the subject between the probe 406 and the region of anisotropic tissue 405. Similarly, the position tracking system 416 is shown positioned on a lower surface of the anisotropic tissue 405, however it is to be understood that there may be one or more materials such as other tissues of the subject, clothing of the subject, air, bedding, etc. between the position tracking system 416 and the anisotropic tissue 405.

The reference plane, the probe 406, the position tracking system 416, and the target plane may each be associated with a coordinate system. The coordinates may be 3D coordinates, such as xyz coordinates. Other coordinate systems (e.g., polar coordinates) may be used in other examples. The coordinate systems may be used to define a position of their respective plane in space. For example, as shown in FIGS. 4A, the reference plane lies along the x and y axes of reference coordinate system 442. The position of the reference plane, probe 406, position tracking system 416, and target plane may each be tracked within their respective coordinate systems, and transformations based on the positions of the coordinate systems used to determine the positions of these elements with respect to each other.

The position tracking coordinate system 440 (or world coordinate system) may be xyz coordinates denoted as x_world, y_world, and z_world. The position tracking coordinate system 440 may be aligned with a position of the position tracking system 416, which may have a known position in relation to the subject (e.g., a predetermined placement in an exam room or determined intra-operatively using registration methods known in the art, such as rigid point-based registration method). The position tracking coordinate system 440 may thus be used to describe a position with respect to position tracking system 416 and therefore to the subject.

The reference coordinate system 442 may be xyz coordinates denoted as x_ref, y_ref, and z_ref. As described herein, the reference coordinate system 442 may align with anatomical features of the anisotropic tissue 405 and/or be selected by a user. By using a known relationship between the reference coordinate system 442 and the world coordinate system 440, a position of the tissue may be known with respect to the position tracking system. A transformation $^{world}T_{ref}$ may be determined to transform coordinate information from the reference coordinate system 442 to the world coordinate system 440. Once the transformation has been determined, the subject may need to remain in a fixed position with relation to the position tracking system 416 (e.g., by lying still).

One or more target planes may be defined with respect to the reference plane. Each of the target planes may have a target coordinate system 444. The target coordinate system 444 may be an xyz coordinate system with axes denoted as x_target, y_target, z_target. A transformation $^{ref}T_{target}$ may be determined to transform coordinate information from the target coordinate system 444 to reference coordinate system 442. By linking the target coordinate system to the reference coordinate system 442 (which in turn is linked to the position tracking coordinate system 440), a position of each of the target planes can be determined with respect to the position tracking system 416.

The current position of the probe 406 may be expressed in the current coordinate system 446. The current coordinate system 446 may be linked to a position of the probe 406 and may move as the probe 406 moves. The current coordinate system 446 may be an xyz coordinate system with axes denoted as x_current, y_current, z_current. As shown in FIG. 4A, the current coordinate system 446 is aligned with the reference coordinate system (442). As shown by the arrow of FIG. 4A, the reference coordinate system 442 may be transformed to the world coordinate system 440 with the function $^{world}T_{ref}$. As shown in FIG. 4B, the current coordinate system 446 has been rotated by about 90° to align with the target coordinate system 444. A transformation between the current coordinate system 446 and world coordinate system 440 may be determined by transformation $^{world}T_{current}$. This transformation may be determined by the position tracking system 416.

A processor of the ultrasound system (e.g., processor 126 of FIG. 1) may use transformations between the coordinate systems to produce directions for positioning the probe 406. The processor may generate a transformation of the current imaging plane position with respect to the target plane position according to equation 1:

$$^{target}T_{current}=(^{ref}T_{target})^{-1}(^{world}T_{ref})^{-1}\,^{world}T_{current} \qquad \text{Equation1}$$

The processor may calculate the position of the current imaging plane to the position of the target plane in real time. As described herein, the processor may generate feedback or instructions to adjust the position of the imaging plane to reduce a difference between the position of the current imaging plane and the position of the target plane. The processor may calculate the difference between the position of the imaging plane and the position of the target plane based on the transformation $^{target}T_{current}$. As described herein, a display (e.g., display 120 of FIG. 1) may display feedback (e.g. visual indicators 122 of FIG. 1) based on the calculated difference as the calculated difference changes in real-time.

The general transformation of Equation 1 may be used to generate specific instructions for adjusting a position of the probe 406. In the example shown in FIGS. 4A-4B, the target plane coordinate system 444 is rotated 90° with respect to the reference plane coordinate system 442 about their mutual y-axis y_ref/y_target. In other words, there is a 90° angle between x_ref, and x_target and between z_ref and z_target. In this example, the only position change the imaging plane needs to undergo is a rotation. The angle β between the current probe position (as determined by current probe coordinate system 446) and the target coordinate system 444 may be determined by:

$$\beta=\cos^{-1}(\hat{x}^Tx_{target}),\text{ where} \qquad \text{Equation 2}$$

$$\hat{x}=\text{proj}(^{target}R_{current}x_{current},XZ_{target}) \qquad \text{Equation 3}$$

where $^T$ is the transpose operator, $^{target}R_{current}$ is the rotation component of the transformation matrix $^{target}T_{current}$, $\hat{x}$ is a projection of a transformed column unit vector along x_current onto the plane $XZ_{target}$ which is the plane defined along axes x_target and z_target of the target coordinate system 444; $\hat{x}$ is normalized. The angle β may be calculated in real time, and may be presented to a user in one or more visual indicators (e.g., visual indicators 122 of FIG. 1). Although in this example the position of the target plane and current imaging plane may only vary by an angle β, additional angles and/or other position elements may be calculated based on the transformations. In some examples, 3 rotational angles and 3 location vectors may be calculated in order to provide 3D/6DOF position information.

Figures 5A, 5B:
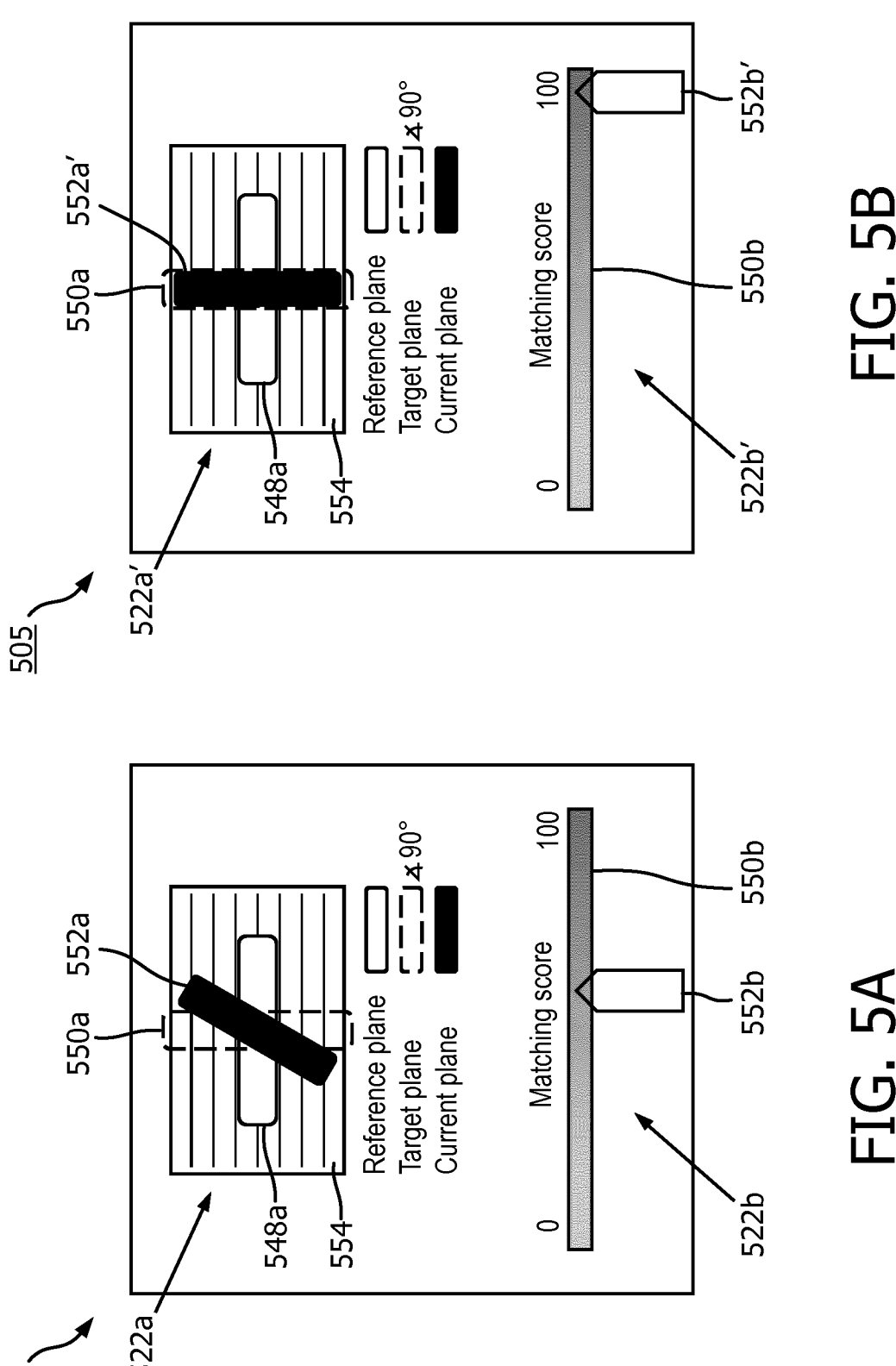
FIGS. 5A, 5B and 5C are graphical user interface elements providing visual indicators in accordance with some examples of the present disclosure.
Figure 5C:
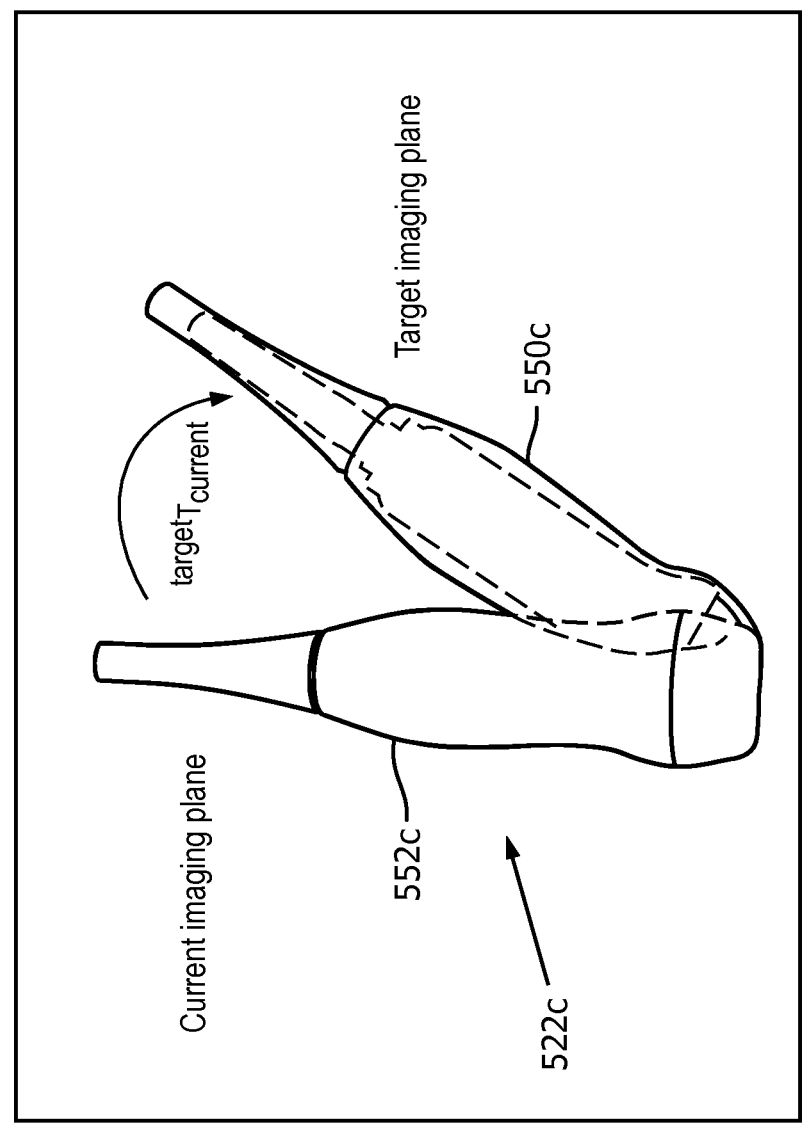
Figure 5C:

FIGS. 5A-5C depict graphical user interface (GUI) elements 500, 505, and 510 comprising visual indicators in accordance with some examples of the present disclosure. The visual indicators may be generated in real-time and may provide guidance to an operator on how to reposition or manipulate the probe in order to acquire one or more target image planes. In some examples, the visual indicators may include instructions for repositioning the probe such that an imaging plane of the probe aligns with the target image plane and thus an image of the subject at the target image plane can be acquired. The visual indicators may also provide feedback about the current position of the imaging plane with respect to the reference plane and to one or more target planes. FIGS. 5A-5C show visual indicators 522*a-c*, reference indicators 548*a*, target indicators 550*a-c*, current indicator 552*a-c*, and tissue indicator 554*a*. The visual indicators in the examples herein may be used to implement any of the visual indicators of the present disclosure (e.g., visual indicator 122 of FIG. 1). The components and arrangement thereof shown in FIGS. 5A-5C are merely illustrative, and other variations, including eliminating components, combining components, rearranging components, and substituting components are all contemplated.

FIGS. 5A-5C depict example visual indicators 522*a-c*, which may be used to guide alignment of the current imaging plane with a target plane. FIGS. 5A and 5B each depict two visual indicators 522*a,b* when the current imaging plane is in a first and second position, respectively. The visual indicators of FIG. 5B are noted as 522*a'* and 522*b'* to indicate the changed position. FIG. 5C depicts a visual indicator 522*c* in accordance with further examples. Any of the visual indicators 522*a-c* may be provided on displays (e.g., as GUI elements 500, 505, 510 of a graphical user interface). Any of the visual indicators 522*a-c* may include a reference indicator 548 configured to depict a position of the reference plane, a target indicator 550 configured to depict a position of the target plane, a current indicator 552 configured to depict a current position of the imaging plane, a tissue indicator 554 configured to depict a property of the tissue (e.g., a fiber orientation of the tissue), or combinations thereof. Notably, in some examples and as described further below, the current indicator may be configured to dynamically update (e.g., as the operator moves the probe) such that it provides a visual indication at any given time the relative angle between the target image plane and the current image plane (i.e., the image plane of the probe at the current position of the probe) or some quantitative or qualitative measure of how close the current image plane is to the target image plane.

In the illustrated example, visual indicator 522*a* includes a reference indicator 548*a*, a target indicator 550*a*, and a current indicator 552*a* in the form of rectangular bars illustratively represent the footprint of the imaging array or of the probe (e.g., probe 106 of FIG. 1). In some examples, the rectangular bar for each of the different indicators may be slightly differently represented. For example, the indicators (in this case, rectangular bar) associated with the reference image plane may be displayed in one color, while the indicators associated with the other image planes may be represented in different colors or in some cases, one or more may be represented as an outline, while others are filled in. In the specific illustrated example, the rectangular bar for the target indicator 550*a* is shown as an outline, while the rectangular bar for the current indicator 552*a* is shown as a filled-in bar. When the operator has positioned the probe so as to align with the target plane (as shown in FIG. 5B), the filled-in bar aligns with and fills the outline of the target indicator. In other examples, the indicators may be differently configured, e.g., the target or the current indicator may be longer, in one or both dimension that the other indicator(s). In other examples, the indicators may be differently distinguished from one other, such as being different colors and/or have different borders (e.g., solid border, dashed border, dotted border, etc.). In some examples, a legend may be provided to aid in distinguishing between the indicators.

In this example, the indicators are overlaid on a tissue indicator 554, which may include one or more lines to represent the direction of fibers of the anisotropic tissue (e.g., fiber 334 of FIG. 3). In this example, the visual indicator 522*a* depicts a simulated top down view (e.g., looking down an axis of a probe towards the tissue), where the target plane is rotated about 90° with respect to the reference plane. The visual indicator 522*a* thus shows target indicator 550*a* rotated about 90° from the reference indicator 548*a*. The system may update the current indicator 552*a* in real time to depict a current position of the imaging plane.

The visual indicator 522*b* shows the current position of the probe, represented by current indicator 552*b*, along a target indicator 550*b*, which is a numerical scale. The target indicator 550*b* may be a normalized value or score (e.g., between 0-100) representing how close the current position of the imaging plane is to the current target plane. Thus, one end of the target indicator 550*b* may represent full alignment of the current plane with the target plane (e.g., a score of 100), while the other end of the scale (e.g., a score of 0) may represent the current plane being totally out of alignment (e.g., orthogonal to the target plane). The current indicator 552*b* may be provided in the form of an arrow or a slider bar, which moves along the target indicator 550*b* to represent the current positioning of the image plane with respect to target plane.

Visual indicator 552*c* shows a current indicator 552*c* and a target indicator 550*c* that are both renderings of a 3D shape of a probe. The 3D renderings may be realistic depictions of the probe, or may be stylized. The current indicator 552*c* may be a solid rendering representing a current position of the probe. The target indicator 550*c* may be a translucent (or wireframe) model of a position of the probe such that when the probe is in the position, the imaging plane produced by the probe aligns with the target plane. The target indicator 550*c* may be rendered in a different color than the current indicator 552*c*, and may change color in response to a changing position of the probe. An arrow may be displayed representing a recommended motion (e.g., a tilt) of the probe to match the target indicator 550*c*.

The instructions and feedback of the visual indicators 522*a-c* may be used to adjust the position of the probe until the current indicator 552*a-c* matches the target indicator 550*a-c*. The system may provide feedback (e.g., a change in color, a tone, or a displayed message) to indicate that the current imaging plane is aligned with a target plane (or within an acceptable tolerance of alignment). The system may prompt a user to record a shear wave elastography image at this point and/or the system may automatically record a shear wave elastography image. The visual indicator(s) 522*a-c* may then update to display a new target plane with target indicator 550*a-c*, or may indicate that a measurement sequence is complete.

As an example, FIG. 5A shows two visual indicators 522*a* and 522*b* each presenting the current position of the same probe. In both cases, the current indicators 552a, 552b indicate that the probe is currently not in alignment with the target probe. Visual indicator 522a shows a simplified 2D representation of the probe position (as if from a top down view) and shows that the current indicator 552a is not aligned with the target indicator 550a. Visual indicator 522b shows the current indicator 552b along a target indicator 550b which is a numerical axis below a maximum value (e.g., 100) which represents alignment with the target plane. FIG. 5B shows the same two visual indicators 522a' and 522b' which reflect a new position of the probe where the imaging plane is in alignment with the target plane. In the case of visual indicator 522a', the current indicator 552a' is now within the target indicator 550a, which is an outline indicating a position of the probe where the imaging plane aligns with the target plane. In the case of visual indicator 522b', the current indicator 552b' has increased along the target indicator 550b (numerical scale) until it is at or about the maximum value. In yet further examples, guidance may be additionally or alternatively provided with non-visual cues. For example, in addition to the visual indicators, the system may be configured to provide tactile or audible indicators (e.g., emit a beep or other sound), when the system has determined that the probe is positioned such that the imaging plane of the probe sufficiently aligns with the target plane (e.g., a position corresponding to the current indicator 552b located anywhere between 90-100).

FIGS. 6A-6B are example displays including shear wave elastography images in accordance with some embodiments of the present disclosure. The images may be presented on a display to a user (e.g., on display 120 of FIG. 1) and/or may be stored in a memory of the system (e.g., memory 130) for later analysis. FIGS. 6A-6B depict images 624, 624' and position indicators 654, 654'. The images 624, 624' may be an implementation of the images 124 of FIG. 1 in certain embodiments. The components shown in FIGS. 6A-6B are merely illustrative, and other variations, including eliminating components, combining components, rearranging components, and substituting components are all contemplated.

FIGS. 6A and 6B show example images 624, 624' that may be presented on a display (such as display 120 of FIG. 1). The images 624, 624' may be presented live to a user and/or may be saved (such as on memory 130 of FIG. 1) for later review. Position information for the position of the image plane at the time each of the images 624, 624' may be calculated and saved along with the images 624,624'. The images 624, 624' may include position indicators 654, 654' which indicate the position of the imaging plane shown in the image 624, 624' with respect to a reference plane. FIG. 6A shows an image 624 aligned with a reference plane, as indicated by position indicator 654, and FIG. 6B shows an image 624' aligned orthogonal to that reference plane as indicated by position indicator 654'. The position indicators 654, 654' may be overlaid on top of the image 624, 624'. The position indicators 654, 654' may be text, or may be some other representation of the position such as a graphical display or a normalized score.

Figures 7A, 7B:
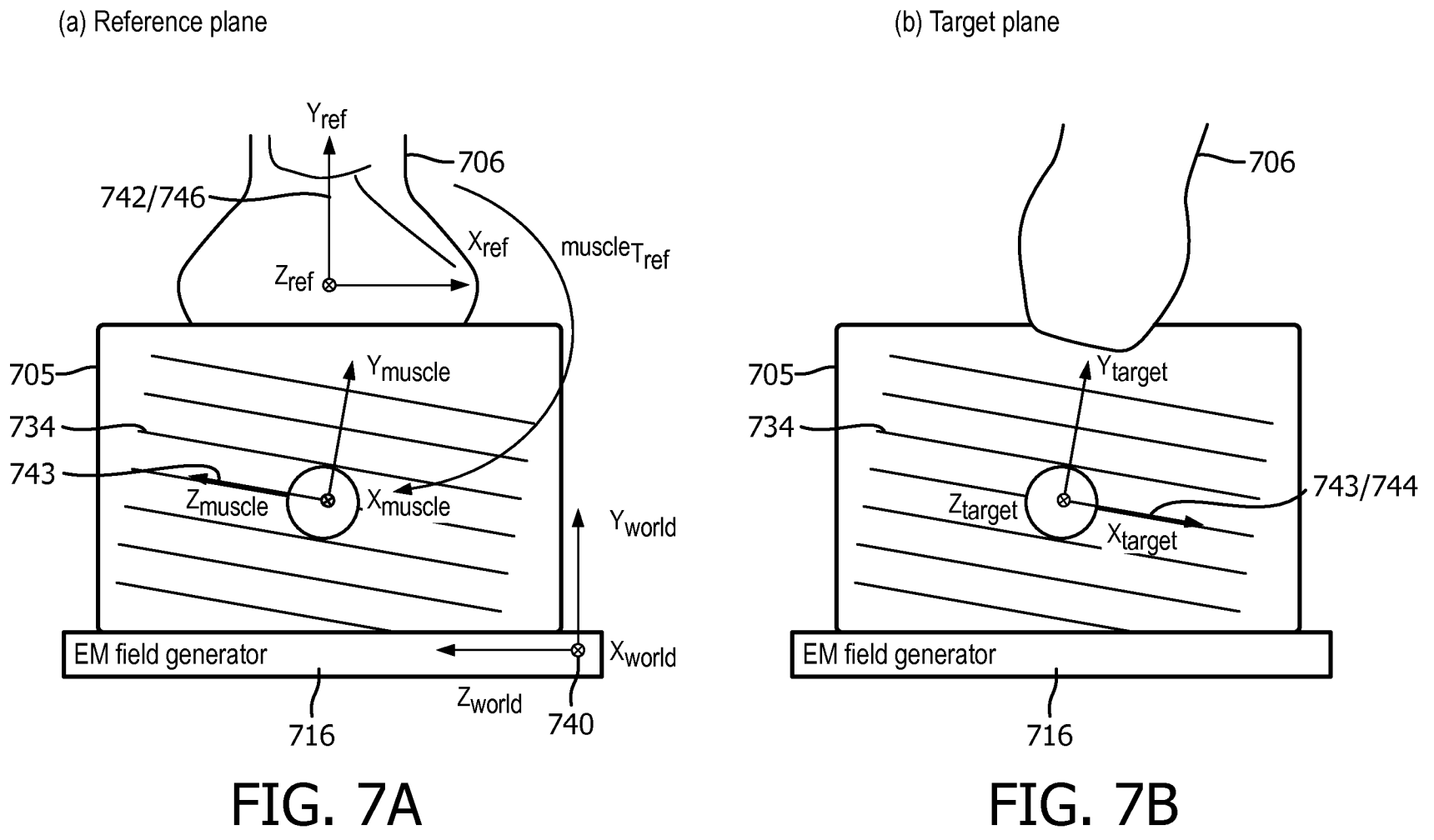

FIGS. 7A-7B are block diagrams of coordinate systems defined by the probe placement and an orientation of the anisotropic tissue arranged in accordance with some embodiments of the present disclosure. An orientation of the tissue may be taken into account when determining positions of the imaging plane in order to account for changes in a direction of the tissue (e.g., changing orientation of fibers of the tissue). FIGS. 7A-7B depict anisotropic tissue 705, probe 706, fibers 734, position tracking system 716, position (or world) coordinate system 740, reference coordinate system 742, target coordinate system 744, current coordinate system 746, and tissue coordinate system 743, which is aligned with the muscle fibers. The probe 706 may be an implementation of the probe 106 of FIG. 1 in certain embodiments. The components shown in FIGS. 7A-7B are merely illustrative, and other variations, including eliminating components, combining components, rearranging components, and substituting components are all contemplated.

The coordinate systems of FIGS. 7A-7B may be generally similar to the coordinates described in FIGS. 4A-4B, except that FIGS. 7A-7B introduce tissue coordinate system 743 to describe a location of the anisotropic tissue 705 fibers. The tissue coordinate system 743 may be an xyz coordinate system including x_tissue, y_tissue, and z_tissue. In the example shown in FIGS. 7A-7B, the tissue is muscle tissue, and so the tissue coordinate system 743 is a muscle coordinate system including x_muscle, y_muscle, and z_muscle. Although muscle is specified here, it is to be understood that the tissue coordinate system may align to any type of anisotropic tissue. The anisotropic tissue 705 may have elements, such as fibers 734, which are not aligned along any of the world coordinate system 740, reference coordinate system 742, and/or target coordinate system 744. The orientation of the fibers 734 may change along a length of the anisotropic tissue 705. The tissue coordinate system 743, which in this case aligns with the fibers 734, may therefore also change along a length of the tissue 705. The tissue coordinate system 743 may be defined by a user. The tissue coordinate system 743 may be generated automatically be extracting the orientation of fibers 734 from the images, such as with the Hough transform, segmentation and parameterization of the fibers 734, and/or backscattering acoustic properties. The target plane may be chosen to align with the fibers 734. When there is a separate tissue coordinate system 743, Equation 1, which defines a transformation between target and current coordinates, may be modified to Equation 4:

$$^{target}T_{current} = ^{target}T_{muscle}\ ^{muscle}T_{ref}$$
$$(^{world}T_{ref})^{-1}\ ^{world}T_{current}$$

Equation 4 where $^{world}T_{current}$ is a transformation between the current coordinate system 746 and the world coordinate system 740, and the $^{target}T_{muscle}$ is a transformation between the tissue coordinate system 743 and the target coordinate system 744. Further calculations may be made to generate specific instructions such as specific angles or location changes between elements of the target coordinate system 744 and the current coordinate system 746, similar to the instructions of Equations 2 and 3.

FIGS. 7A and 7B show probe 706 being rotated to align with a target plane. In the example shown, the target plane is aligned with fibers 734 of the anisotropic tissue 705. FIG. 7A shows the probe 706 aligned with the reference plane (e.g., the current coordinate system 746 and the reference coordinate system 742 are aligned). In this example, the probe 706 may need to undergo two rotations (about y_ref and about z_ref) to align a current imaging plane with the target plane. FIG. 7B shows the probe 706 aligned with the target coordinate system 744. The transformation calculated in Equation 4 may be used to generate instructions for the needed position changes of the probe 706 in real-time, and allows target planes to be selected along different points of a tissue with different orientations of fibers 734.

FIG. 8 is a flow chart depicting a multi-angle shear wave imaging in accordance with certain embodiments of the present disclosure. The example method 800 shows steps that may be utilized, in any sequence, by the systems and/or apparatuses described herein. The method may be performed by an ultrasound system, such as the ultrasound system 112 of FIG. 1. In some embodiments, the method 800 may be implemented in the instructions 132 of a system 112 and executed by a processor 126.

In the embodiment shown, the method 800 begins at block 810 by "Determining a position of an imaging plane of a probe with respect to anisotropic tissue based on position tracking data generated based, at least in part, on sensor data received from a position sensor coupled to the probe."

At block 820, the method involves "Defining at least one target plane."

At block 830, the method involves "Determining a difference between the position of the imaging plane and a position of and the at least one target plane."

At block 840, the method involves "Providing a visual indicator of the determined difference on a display and dynamically updating the visual indicator responsive to a change in the position of the imaging plane."

At block 850, the method involves "Producing at least one shear wave image of the target plane with the transducer."

The method 800 may also include generating instructions to adjust a position of the imaging plane. The instructions may be provided to a user, such as via visual indicators 122 of FIG. 1. The user may adjust a position of the probe in response to the instructions, and may receive additional feedback as the adjusting continues. The instructions may also be used to automatically adjust a position of the imaging plane, such as by changing a position of the probe and/or by changing a position of the imaging plane relative to the probe. The position of the probe may be changed, for example, with actuators controlled by a controller (such as controller 128 of FIG. 1). The position of the imaging plane relative to the probe may be changed by, for example, moving a transducer within the plane, or using beam steering.

Steps of the method 800 may be repeated. For example the blocks 820-850 may be repeated for a plurality of target planes at different positions about the tissue. Steps of the method 800 may run continuously, such as blocks 810, or may be executed in response to input, such as block 850, which may, for example, be triggered by a user, or may be triggered when the system detects certain conditions (such as the measured difference between the imaging plane and target plane falling below a threshold) have been met.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system for shear wave imaging comprising:

a probe configured to acquire ultrasound echo signals for producing shear wave images of anisotropic tissue of a subject, wherein the probe is configured to be coupled to a position tracking system for tracking a position of the probe with respect to the subject;

a processor in communication with the probe and configured to receive position tracking data from the position tracking system, wherein the processor further is configured to:

define at least one target plane in the anisotropic tissue at an a first angle with respect to and using a reference plane of the anisotropic tissue;

determine a second angle between a position of an imaging plane of the probe as indicated by the position tracking data and the reference plane;

define a first transformation between a position of the at least one target plane and the reference plane based, at least in part, on the first angle;

define a second transformation between the position of the image plane and the reference plane based, at least in part, on the second angle;

determine a difference between the position of the image plane and the position of the target plane using the first and second transformations; and provide a visual indicator of the difference on a display of the ultrasound system, wherein the processor is configured to dynamically update the visual indicator responsive to a change in the position of the imaging plane with respect to the target plane.

2. The ultrasound imaging system of claim 1, wherein the processor is further configured to cause at least one shear wave image to be automatically generated when the difference between the first and second positions is below a threshold.

3. The ultrasound imaging system of claim 1, wherein the position tracking system is configured to determine a spatial location of the probe and a rotation of the probe with respect to the reference plane.

4. The ultrasound imaging system of claim 1, wherein the probe comprises at least one sensor configured to receive information from the position tracking system to dynamically determine the position of the probe.

5. The ultrasound imaging system of claim 4, wherein the position tracking system comprises an electromagnetic field generator and the at least one sensor comprises at least one electromagnetic sensor attached to the probe.

6. The ultrasound imaging system of claim 5, wherein the at least one electromagnetic sensor is embedded in the probe.

7. The ultrasound imaging system of claim 1, wherein the processor is configured to receive an indication of the reference plane responsive to user input.

8. The ultrasound imaging system of claim 7, further comprising a reference plane selector, and wherein the processor is further configured to set the reference plane to a current imaging plane of the probe responsive to activation of the reference plane selector.

9. The ultrasound imaging system of claim 1, wherein the processor is configured to determine the reference plane based on a direction of fibers of the anisotropic tissue.

10. The ultrasound imaging system of claim 9, wherein the processor is configured to set the reference plane such that it is aligned with the direction of the fibers of the anisotropic tissue.

11. The ultrasound imaging system of claim 9, wherein the anisotropic tissue is selected from musculoskeletal tissue, myocardium tissue, vascular wall tissue, and thyroid tissue and wherein the processor is configured to estimate the direction of fibers of the musculoskeletal tissue, myocardium tissue, vascular wall tissue, or thyroid tissue.

12. The ultrasound imaging system of claim 11, wherein the processor is further configured to estimate the direction of the fibers based at least in part on a three dimensional (3D) image of the anisotropic tissue.

13. The ultrasound imaging system of claim 1, wherein the processor is further configured to define the at least one target plane at a predetermined angle with respect to the reference plane.

14. The ultrasound imaging system of claim 13, wherein the processor is configured to define a plurality of target planes at predetermined angular intervals with respect to the reference plane.

15. The ultrasound imaging system of claim 14, wherein the visual indicator comprises a numerical scale with a dynamic component configured to move along the scale responsive to changes in the determined difference.

16. The ultrasound imaging system of claim 1, wherein the processor is further configured to generate instructions for adjusting the position of the probe, wherein the instructions are configured to reduce the difference between the first and second position.

17. The ultrasound imaging system of claim 16, wherein the processor is further configured to control an actuator for automatically adjusting the position of the probe based on the instructions.

18. The ultrasound imaging system of claim 16, wherein the visual indicator comprises a current plane indicator and a target plane indicator, wherein the current plane indicator is dynamically adjusted by the processor responsive to changes in the position of the probe with respect to the target plane.

19. The ultrasound imaging system of claim 18, wherein the current plane indicator is a visual representation of a current imaging plane of the probe.

20. The ultrasound imaging system of claim 18, wherein the target plane indicator is a visual representation of an imaging plane corresponding to the target plane.

21. A method of shear wave imaging, the method comprising:

determining a position of an imaging plane of a probe with respect to anisotropic tissue based on position tracking data generated based, at least in part, on sensor data received from a position sensor coupled to the probe;

defining a reference plane in the anisotropic tissue;

defining at least one target plane using the reference plane and an a first angle between the at least one target plane and the reference plane;

determining a second angle between the position of the imaging plane and the reference plane;

defining a first transformation between a position of the at least one target plane and the reference plane based, at least in part, on the first angle;

defining a second transformation between the position of the image plane and the reference plane based, at least in part, on the second angle;

determining a difference between the position of the image plane and the position of the tar g et plane using the first and second transformations;

providing a visual indicator of the determined difference on a display and dynamically updating the visual indicator responsive to a change in the position of the imaging plane; and producing at least one shear wave image of the target plane with the probe.

22. The method of claim 21; further comprising adjusting the position of the imaging plane to align it with the position of the target plane.

23. The method of claim 21, further comprising displaying the determined position of the imaging plane on the at least one shear wave image produced at the determined position.

24. The method of claim 21, further comprising generating instructions for adjusting the position of the imaging plane, wherein the instructions are configured to reduce the determined difference.

25. The method of claim 24, further comprising sending the generated instructions to an actuator configured to control the position of the imaging plane.

26. The method of claim 24, further comprising adjusting the position of the imaging plane based on the generated instructions.

27. The method of claim 26, wherein the adjusting the position of the imaging plane comprises adjusting a location of the probe, adjusting at least one angular orientation of the probe, or combinations thereof.

\* \* \* \* \*